(12) United States Patent
Kurasawa et al.

(10) Patent No.: US 9,486,446 B2
(45) Date of Patent: Nov. 8, 2016

(54) ORALLY DISINTEGRATING SOLID PREPARATION

(75) Inventors: Takashi Kurasawa, Osaka (JP); Yasuko Watanabe, Osaka (JP); Yohko Akiyama, Ohmihachiman (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1053 days.

(21) Appl. No.: 12/521,488

(22) PCT Filed: Dec. 27, 2007

(86) PCT No.: PCT/JP2007/075179
§ 371 (c)(1),
(2), (4) Date: Jun. 26, 2009

(87) PCT Pub. No.: WO2008/081891
PCT Pub. Date: Jul. 10, 2008

(65) Prior Publication Data
US 2010/0316709 A1    Dec. 16, 2010

(30) Foreign Application Priority Data
Dec. 28, 2006  (JP) .............................. 2006-356405

(51) Int. Cl.
| | | |
|---|---|---|
| *A61K 9/00* | (2006.01) | |
| *A61K 9/20* | (2006.01) | |
| *A61K 9/50* | (2006.01) | |
| *A61K 31/444* | (2006.01) | |
| *A61K 31/4439* | (2006.01) | |

(52) U.S. Cl.
CPC ......... *A61K 31/4439* (2013.01); *A61K 9/0056* (2013.01); *A61K 9/2081* (2013.01); *A61K 9/5026* (2013.01); *A61K 9/5047* (2013.01); *A61K 9/5084* (2013.01); *A61K 31/444* (2013.01)

(58) Field of Classification Search
None
See application file for complete search history.

(56) References Cited

U.S. PATENT DOCUMENTS

| | | | |
|---|---|---|---|
| 4,971,805 A * | 11/1990 | Kitanishi et al. | .............. 424/494 |
| 5,026,560 A | 6/1991 | Makino et al. | |
| 5,057,317 A * | 10/1991 | Iida | ................ 424/423 |
| 5,464,632 A | 11/1995 | Cousin et al. | |
| 5,516,531 A | 5/1996 | Makino et al. | |
| 6,328,994 B1 | 12/2001 | Shimizu et al. | |
| 2001/0010825 A1* | 8/2001 | Shimizu et al. | .............. 424/465 |
| 2002/0142034 A1 | 10/2002 | Shimizu et al. | |
| 2004/0018235 A1 | 1/2004 | Tanizawa et al. | |
| 2004/0109890 A1 | 6/2004 | Sugimoto et al. | |
| 2005/0003005 A1* | 1/2005 | Shimizu et al. | .............. 424/471 |
| 2008/0292701 A1 | 11/2008 | Shimizu et al. | |
| 2011/0081412 A1 | 4/2011 | Shimizu et al. | |

FOREIGN PATENT DOCUMENTS

| | | |
|---|---|---|
| EP | 0 277 741 | 8/1988 |
| EP | 1 967 211 | 9/2008 |
| JP | 5-92918 | 4/1993 |
| JP | 2000-281564 | 10/2000 |
| JP | 2005-139086 | 6/2005 |
| WO | 99/59544 | 11/1999 |
| WO | 2006/036007 | 4/2006 |

OTHER PUBLICATIONS

Shimizu, T., "Formulation Study for Lansoprazole Fast-disintegrating Tablet. III. Design of Rapidly Disintegrating Tablets", Chem. Pharm. Bull., 2003, pp. 1121-1127.*
Low Substituted Hydroxypropyl Cellulose NF L-HPC Functional Disintegrant, ShinEtsu Chemical Co., Ltd., Cellulose & Pharmaceutical Excipients Department, http://www.metolose.jp/e, 23 pages.
Cech, et al., "Influence of Plasticizers on the Film Properties of HPMC and PVA and Comparison of the Results with the Properties of Kollicoat® IR as a single Film Former", BASF the Chemical Company, ExcipientFest Europe, Jun. 17-18, 2008, 1 page.
Eudragit®—Application Guildlines 11th edition, EVONIK Industries, Sep. 2009, 168 pages.

\* cited by examiner

*Primary Examiner* — Michael G Hartley
*Assistant Examiner* — Lance Rider
(74) *Attorney, Agent, or Firm* — Hamre, Schumann, Mueller & Larson, P.C.

(57) ABSTRACT

The present invention provides an orally-disintegrating solid preparation comprising fine granules showing controlled release of a pharmaceutically active ingredient, wherein the outermost layer of the fine granules is coated with a coating layer comprising hydroxypropylmethylcellulose and low-substituted hydroxypropylcellulose and breakage of the fine granules during tableting is suppressed.

15 Claims, No Drawings

ORALLY DISINTEGRATING SOLID PREPARATION

TECHNICAL FIELD

The present invention relates to an orally-disintegrating solid preparation comprising fine granules showing controlled release of a pharmaceutically active ingredient, wherein the outermost layer of the fine granules is coated with a coating layer comprising hydroxypropylmethylcellulose (HPMC) and low-substituted hydroxypropylcellulose (L-HPC), and a method of suppressing breakage of fine granules during tableting, which comprises coating the outermost layer of the fine granules in an orally-disintegrating tablet produced by tableting the fine granules showing controlled release of a pharmaceutically active ingredient and an additive, with a coating layer comprising hydroxypropylmethylcellulose (HPMC) and low-substituted hydroxypropylcellulose (L-HPC) and the like.

BACKGROUND OF THE INVENTION

With an aging population and changes in life environment, the development of an orally-disintegrating solid preparation, which can be taken easily and readily at any time and anywhere without taking water, and which retains convenience of handling characterizing tablets, is desired.

On the other hand, when a physiologically active substance is a substance having a bitter taste, masking of the bitter taste by coating is preferable for drug compliance. Also, when the physiologically active substance is easily decomposed by an acid, it is necessary to coat the ingredient to prevent decomposition by the gastric acid and ensure sufficient delivery to the intestine. To solve these problems, coated tablets, capsules and the like are generally used.

To meet these requirements, tablets containing coated fine granules have conventionally been developed. For example, JP-A-6-502194 (U.S. Pat. No. 5,464,632) discloses a rapidly disintegratable multiparticular tablet comprising an effective substance in the form of coated fine particles and the like. In addition, JP-A-2000-281564 and JP-A-2000-103731 disclose orally-disintegrating tablets containing coated fine granules in tablets.

During the production of solid preparations such as tablet containing coated fine granules and the like, however, fine granules may be broken during tableting as evidenced by partial destruction of a coated film of fine granules and the like, resulting in problems such as a decreased masking effect on the aforementioned bitter taste, acid resistance and the like.

patent document 1: JP-A-6-502194
patent document 2: JP-A-2000-281564
patent document 3: JP-A-2000-103731

DISCLOSURE OF THE INVENTION

Problems to be Solved by the Invention

The present invention aims to suppress, during tableting, breakage of fine granules showing controlled release of a pharmaceutically active ingredient, in the production of an orally-disintegrating solid preparation containing the fine granules (tablet, etc.).

Means of Solving the Problems

The present inventors have found that breakage of fine granules during tableting can be reduced by coating the outermost layer of the fine granules in an orally-disintegrating solid preparation (tablet etc.) produced by tableting the fine granules showing controlled release of a pharmaceutically active ingredient and an additive, with a coating layer comprising hydroxypropylmethylcellulose (to be sometimes abbreviated as HPMC) and low-substituted hydroxypropylcellulose (to be sometimes abbreviated as L-HPC), which resulted in the completion of the present invention.

Accordingly, the present invention provides the following.

[1] An orally-disintegrating solid preparation comprising fine granules showing controlled release of a pharmaceutically active ingredient, wherein the outermost layer of the fine granules is coated with a coating layer comprising hydroxypropylmethylcellulose and low-substituted hydroxypropylcellulose.
[2] The preparation of [1], wherein a weight ratio of hydroxypropylmethylcellulose and low-substituted hydroxypropylcellulose in the coating layer is 10:1-1:10.
[3] The preparation of [1], wherein the fine granules have a mean particle size of about 500 µm or below.
[4] The preparation of [1], which is prepared using fine granules having a mean particle size of about 500 µm or below.
[5] The preparation of [1], wherein the fine granules comprise a core granule comprising a pharmaceutically active ingredient and a release-controlling film applied on the core granule.
[6] The preparation of [5], wherein the release-controlling film has an enteric coating layer.
[7] The preparation of [5], wherein the core granule further comprises a basic inorganic salt.
[8] The preparation of [6], wherein the enteric coating layer is formed via an intermediate coating layer formed on the core granule.
[9] The preparation of [6], wherein the enteric coating layer comprises a polymer substance that dissolves within a pH range of not less than 6.0 and not more than 7.5.
[10] The preparation of [6], wherein the enteric coating layer comprises a mixture of one or more kinds selected from the group consisting of hydroxypropylmethylcellulose phthalate, cellulose acetate phthalate, carboxymethylethylcellulose, methyl methacrylate-methacrylate copolymer, methacrylate-ethyl acrylate copolymer, methacrylate-methyl acrylate-methyl methacrylate copolymer, hydroxypropylmethylcellulose acetate succinate, polyvinyl acetate phthalate and shellac.
[11] The preparation of [6], wherein the enteric coating layer comprises two or more kinds of coated films that dissolve within different pH ranges, and the coated film comprises a mixture of one or more kinds selected from the group consisting of hydroxypropylmethylcellulose phthalate, cellulose acetate phthalate, carboxymethylethylcellulose, methyl methacrylate-methacrylic acid copolymer, methacrylic acid-ethyl acrylate copolymer, methacrylic acid-methyl acrylate-methyl methacrylate copolymer, hydroxypropylmethylcellulose acetate succinate, polyvinyl acetatephthalate and shellac.
[12] The preparation of [5], wherein the release-controlling film has a diffusion control coating layer.
[13] The preparation of [12], wherein the diffusion control coating layer comprises a mixture of one or more kinds selected from the group consisting of ethyl acrylate-methyl methacrylate trimethylammoniumethyl methacrylate chloride copolymer, methyl methacrylate-ethyl acrylate copolymer and ethylcellulose.

[14] The preparation of [5], wherein the release-controlling film comprises the enteric coating layer and the diffusion control coating layer in combination.
[15] The preparation of [1], wherein the pharmaceutically active ingredient is unstable to acid.
[16] The preparation of [15], wherein the pharmaceutically active ingredient unstable to acid is a proton pump inhibitor.
[17] The preparation of [16], wherein the proton pump inhibitor is a compound represented by the formula (I):

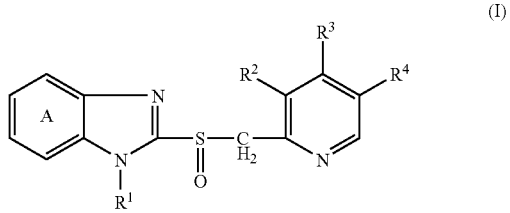

wherein ring A is a benzene ring or pyridine ring optionally having substituent(s), $R^1$ is a hydrogen atom, an aralkyl group optionally having substituent(s), an acyl group or an acyloxy group, $R^2$, $R^3$ and $R^4$ are the same or different and each is a hydrogen atom, an alkyl group optionally having substituent(s), an alkoxy group optionally having substituent(s) or an amino group optionally having substituent(s), or an optically active form thereof or a salt thereof.
[18] The preparation of [16], wherein the proton pump inhibitor is lansoprazole, omeprazole, rabeprazole, Pantoprazole, ilaprazole, tenatoprazole or an optically active form thereof or a salt thereof.
[19] An orally-disintegrating solid preparation comprising (1) fine granules A showing controlled release of a pharmaceutically active ingredient wherein the outermost layer of the fine granules is coated with a coating layer comprising hydroxypropylmethylcellulose and low-substituted hydroxypropylcellulose, and (2) fine granules B with a different release rate of a pharmaceutically active ingredient from that of the fine granules of (1).
[20] The preparation of [19], wherein the pharmaceutically active ingredient of the fine granules A and that of the fine granules B are the same.
[21] The preparation of [19], wherein the fine granules B have a mean particle size of about 500 μm or below.
[22] The preparation of [19], prepared using the fine granules B having a mean particle size of about 500 μm or below.
[23] The preparation of [19], wherein the fine granules B comprise a core granule comprising a pharmaceutically active ingredient and an enteric coating layer formed thereon.
[24] The preparation of [23], wherein the enteric coating layer of the fine granules B comprises a polymer substance that dissolves within a pH range of not less than 5.0 and not more than 6.0.
[25] The preparation of [23], wherein the enteric coating layer of the fine granules B comprises one or more kinds of aqueous enteric polymer material selected from hydroxypropylmethylcellulose phthalate, cellulose acetate phthalate, hydroxypropylmethylcellulose acetate succinate, methacrylic acid copolymer, carboxymethylethylcellulose and shellac.
[26] The preparation of [23], wherein the enteric coating layer of the fine granules B comprises a sustained-release material of a methacrylic acid copolymer.
[27] The preparation of [19], wherein the fine granules A and the fine granules B comprise the pharmaceutically active ingredient at a weight ratio of 1:10-10:1.
[28] The preparation of [19], further comprising an additive besides fine granules.
[29] The preparation of [28], wherein the additive comprises a water-soluble sugar alcohol.
[30] The preparation of [28], wherein the additive comprises a disintegrant.
[31] The preparation of [28], wherein the fine granules A are comprised at 10-50 wt %, the fine granules B are comprised at 10-30 wt %, and the additive is comprised at 20-80 wt %, each relative to the whole preparation.
[32] The preparation of [1] or [19], wherein the total weight of the preparation is about 1000 mg or below.
[33] The preparation of [1] or [19], wherein the oral disintegration time is about 90 seconds or less.
[34] The preparation of [16], which is capable of achieving an average pH in the stomach of not less than 4 at 0.5 hr after oral administration and maintaining said pH or higher pH for 14 hours or longer.
[35] A method of suppressing breakage of fine granules during tableting, which comprises coating the outermost layer of the fine granules in an orally-disintegrating tablet produced by tableting the fine granules showing controlled release of a pharmaceutically active ingredient and an additive, with a coating layer comprising hydroxypropylmethylcellulose and low-substituted hydroxypropylcellulose.

Effect of the Invention

The orally-disintegrating solid preparation of the present invention shows reduced breakage of fine granules during tableting. Therefore, in the solid preparation comprising fine granules comprising a pharmaceutically active ingredient, particularly, a pharmaceutically active ingredient unstable to acid, the release of the pharmaceutically active ingredient in the presence of acid, for example, in the stomach, can be improved, and can be controlled to achieve a desired dissolution profile. In addition, variation of dissolution profiles for preparations or lots (dissolution variation) can also be improved.

Since the orally-disintegrating solid preparation of the present invention can control release of a pharmaceutically active ingredient for a long time, a therapeutically effective concentration can be maintained for a prolonged time, administration frequency can be reduced, and effectiveness of treatment at a low dose and reduction of side effects caused by rise of blood concentration and the like can be ensured.

Since the orally-disintegrating solid preparation of the present invention shows superior disintegration property or dissolution property in the oral cavity, it is used for the prophylaxis or treatment of various diseases as a preparation conveniently taken by elderly persons and children even without water. In addition, since the fine granules comprising the pharmaceutically active ingredient having a size preventing powdery texture are blended, the preparation is smooth in the mouth.

The orally-disintegrating solid preparation of the present invention is explained in detail in the following.

The orally-disintegrating solid preparation of the present invention comprises fine granules showing controlled release of a pharmaceutically active ingredient, wherein the outermost layer of the fine granules is coated with a coating layer comprising hydroxypropylmethylcellulose (HPMC)

and low-substituted hydroxypropylcellulose (L-HPC) (hereinafter sometimes to be referred to as the preparation of the present invention).

A pharmaceutically active ingredient used in the present invention may be in any form of a solid, a powder, a crystal, oil, a solution and the like. Examples of the pharmaceutically actively active ingredient include a revitalizer, an antipyretic analgesic antiphlogistic drugs, a psychotropic agent, an antianxiety agent, an antidepressant, a hypnotic sedative, an antiepileptic drugs, a central nervous system drug, a brain metabolism improving agent, a brain circulation improving agent, an antiepileptic agent, a sympathomimetic stimulant, a gastrointestinal agent, an antacid, an antiulcer agent, an antitussive expectorant, an antiemetic, a respiratory accelerator, a bronchodilator, an antiallergy agent, a dental agent for oral use, an antihistamine, an inotropic agent, an agent for arrhythmia, a diuretic, a blood pressure lowering agent, a vasoconstrictor, a coronary vasodilator, a peripheral vasodilator, an agent for hyperlipemia, a cholagogue, an antibiotic, a chemotherapeutic agent, an agent for diabetes, an agent for osteoporosis, an antirheumatic, a skeletal muscle relaxant, a hormone agent, an alkaloidal narcotic, a sulfa drug, a gout remedy, a blood coagulation inhibitor, an anti-malignant tumor agent, an Alzheimer's disease remedy and the like, and one or more selected from the aforementioned ingredients are used.

Examples of the revitalizer include vitamins such as vitamin A, vitamin D, vitamin E (d-α-tocopherol acetate, etc.), vitamin $B_1$ (dibenzoylthiamine, fursultiamine hydrochloride, etc.), vitamin $B_2$ (riboflavin butyrate, etc.), vitamin $B_6$ (pyridoxine hydrochloride, etc.), vitamin C (ascorbic acid, sodium L-ascorbate, etc.), and vitamin $B_{12}$ (hydroxocobalamin acetate, cyanocobalamin, etc.), minerals such as calcium, magnesium and iron, proteins, amino acids, oligosaccharides, galenicals, and the like.

Examples of the antipyretic analgesic antiphogistic drugs include aspirin, acetaminophen, ethenzamide, ibuprofen, diphenhydramine hydrochloride, dl-chlorphenylamine maleate, dihydrocodeine phosphate, noscapine, methylephedrine hydrochloride, phenylpropanolamine hydrochloride, caffeine, caffeine anhydride, serrapeptase, lysozyme chloride, tolfenamic acid, mefenamic acid, diclofenac sodium, flufenamic acid, salicylamide, aminopyrine, ketoprofen, indometacin, bucolome, pentazocine, and the like.

Examples of the psychotropic agent include chlorpromazine, reserpine, and the like.

Examples of the antianxiety agent include alprazolam, chlordiazepoxide, diazepam, and the like.

Examples of the antidepressant include imipramine, maprotiline hydrochloride, amphetamine, and the like.

Examples of the hypnotic sedative include estazolam, nitrazepam, diazepam, perlapine, phenobarbital sodium, and the like.

Examples of the antiepileptic drugs include scopolamine hydrobromide, diphenhydramine hydrochloride, papaverine hydrochloride, meclizine hydrochloride, dimenthydrinate and the like.

Examples of the central nervous system drug include citicoline, and the like.

Examples of the brain metabolism improving agent include meclofenoxate hydrochloride, and the like.

Examples of the brain circulation improving agent include vinpocetine, and the like.

Examples of the antiepileptic include phenyloin, carbamazepine, and the like.

Examples of the sympathomimetic stimulant include isoproterenol hydrochloride, and the like.

Examples of the gastrointestinal agent include stomachic digestive agents such as diastase, sugar-comprising pepsine, scopolia extract, cellulase AP3, lipase AP, and cinnamic oil, and agents for controlling intestinal function such as berberine chloride, resistant *lactobacillus*, bifidobacteria, and the like.

Examples of the antacid include magnesium carbonate, sodium hydrogen carbonate, magnesium aluminate metasilicate, synthetic hydrotalcite, precipitated calcium carbonate, magnesium oxide, and the like.

Examples of the antiulcer agent include lansoprazole, omeprazole, rabeprazole, pantoprazole, ilaprazole, tenatoprazole, famotidine, cimetidine, ranitidine hydrochloride, and the like.

Examples of the antitussive expectorant include cloperastine hydrochloride, dextromethorphan hydrobromide, theophylline, potassium guaiacolsulfonate, guaifenesin, codeine phosphate, and the like.

Examples of the antiemetic include difenidol hydrochloride, metoclopramide, and the like.

Examples of the respiratory accelerator include levallorphan tartrate, and the like.

Examples of the bronchodilator include theophylline, salbutamol sulfate, and the like.

Examples of the antiallergy agent include amlexanox, seratrodust, and the like.

Examples of the dental agent for oral use include oxytetracycline, triamcinolone acetonide, chlorhexidine hydrochloride, lidocaine, and the like.

Examples of the antihistamine include diphenhydramine hydrochloride, promethazine, isothipendyl hydrochloride, dl-chlorphenylamine maleate, and the like.

Examples of the inotropic agent include caffeine, digoxin, and the like.

Examples of the agent for arrhythmia include procainamide hydrochloride, propranolol hydrochloride, pindolol, and the like.

Examples of the diuretic include isosorbide, furosemide, a thiazide agent such as HCTZ, and the like.

Examples of the blood pressure lowering agent include delapril hydrochloride, captopril, hexamethonium bromide, hydralazine hydrochloride, labetalol hydrochloride, manidipine hydrochloride, candesartan cilexetil, methyldopa, losartan, valsartan, eposartan, irbesartan, tasosartan, telmisartan, and the like.

Examples of the vasoconstrictor include phenylephrine hydrochloride, and the like.

Examples of the coronary vasodilator include carbochromen hydrochloride, molsidomine, verapamil hydrochloride, and the like.

Examples of the peripheral vasodilator include cinnarizine, and the like.

Examples of the agent for hyperlipemia include cerivastatin sodium, simvastatin, pravastatin sodium, and the like.

Examples of the cholagogue include dehydrocholic acid, trepibutone, and the like.

Examples of the antibiotic include cephem antibiotics such as cephalexin, cefaclor, amoxicillin, pivmecillinam hydrochloride, cefotiam hexetil hydrochloride, cefadroxil, cefixime, cefditoren pivoxil, cefteram pivoxil, cefpodoxime proxetil, cefotiam hydrochloride, cefozopran hydrochloride, cefmenoxime hydrochloride, and cefsulodin sodium, synthetic antibacterial agents such as ampicillin, ciclacillin, sulbenicillin sodium, nalidixic acid, and enoxacin, monobactam antibiotics such as carumonam sodium, penem antibiotics, carbapenem antibiotics, and the like.

Examples of the chemotherapeutic agent include sulfamethizole, sulfamethizole hydrochloride, thiazosulfone, and the like.

Examples of the agent for diabetes include tolbutamide, pioglitazone hydrochloride, voglibose, glibenclamide, troglitazone, rosiglitazone maleate, acarbose, miglitol, emiglitate, and the like.

Examples of the agent for osteoporosis include ipriflavone, and the like.

Examples of the skeletal muscle relaxant include methocarbamol, and the like.

Examples of the anti-rheumatic drug include methotrexate, bucillamine and the like.

Examples of the hormone agent include liothyronine sodium, dexamethasone sodium phosphate, predonisolone, oxendolone, leuprorelin acetate, and the like.

Examples of the alkaloidal narcotic include opium, morphine hydrochloride, ipecac, oxycodone hydrochloride, opium alkaloid hydrochloride, cocaine hydrochloride, and the like.

Examples of the sulfa drug include sulfamine, sulfisomidine, sulfamethizole, and the like.

Examples of the gout remedy include allopurinol, colchicine, and the like.

Examples of the blood coagulation inhibitor include dicoumarol, and the like.

Examples of the anti-malignant tumor agent include 5-fluorouracil, uracil, mitomycin, and the like.

Examples of the Alzheimer's disease remedy include idebenone, vinpocetine, and the like.

Among the aforementioned pharmaceutically active ingredients, an antiulcer agent is preferably used.

A preferable pharmaceutically active ingredient is a pharmaceutically active ingredient unstable to acid.

Examples of the "pharmaceutically active ingredient unstable to acid" include compounds which are labile in an acidic region and/or inactivated by an acid, and specific examples thereof include vitamin compounds (vitamin $B_{12}$, fursultiamine, folic acid, vitamin A, vitamin D, etc.), proton pump inhibitor (PPI) and the like. It is particularly preferably proton pump inhibitor (PPI), and a benzimidazole compound represented by the formula (I) and having a known antiulcer activity, an optically active form thereof and a salt thereof and the like can be mentioned.

A compound represented by the formula (I)

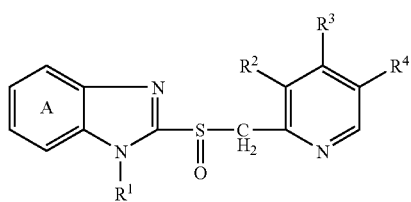

(I)

wherein
ring A is a benzene ring or a pyridine ring, each of which optionally has substituent(s),
$R^1$ is a hydrogen atom, an aralkyl group optionally having substituent(s), an acyl group or an acyloxy group, and
$R^2$, $R^3$ and $R^4$ are the same or different and each is a hydrogen atom, an alkyl group optionally having substituent(s), an alkoxy group optionally having substituent(s) or an amino group optionally having substituent(s),
or an optically active form thereof or a salt thereof.

The compound is preferably a compound wherein, in the formula (I),
ring A is a benzene ring or a pyridine ring, each of which optionally has substituent(s) selected from a halogen atom, an optionally halogenated $C_{1-4}$ alkyl group, an optionally halogenated $C_{1-4}$ alkoxy group and a 5- or 6-membered heterocyclic group,
$R^1$ is a hydrogen atom,
$R^2$ is a $C_{1-6}$ alkyl group, a $C_{1-6}$ alkoxy group, a $C_{1-6}$ alkoxy-$C_{1-6}$ alkoxy group or a di-$C_{1-6}$ alkylamino group,
$R^3$ is a hydrogen atom, a $C_{1-6}$ alkoxy-$C_{1-6}$ alkoxy group or an optionally halogenated $C_{1-6}$ alkoxy group, and
$R^4$ is a hydrogen atom or a $C_{1-6}$ alkyl group.

In the above-mentioned compound represented by the formula (I), examples of the "substituent" of the "benzene ring or pyridine ring, each of which optionally has substituent(s)" for ring A include a halogen atom, a cyano group, a nitro group, an alkyl group optionally having substituent(s), a hydroxy group, an alkoxy group optionally having substituent(s), an aryl group, an aryloxy group, a carboxy group, an acyl group, an acyloxy group, a 5- to 10-membered heterocyclic group and the like. The benzene ring or pyridine ring optionally has 1 to 3 of these substituents. When the number of the substituents is not less than 2, respective substituents may be the same or different. Of these substituents, a halogen atom, an alkyl group optionally having substituent(s), an alkoxy group optionally having substituent(s) and the like are preferable.

Examples of the halogen atom include fluorine, chlorine, bromine atom and the like. Of these, fluorine is preferable.

Examples of the "alkyl group" of the "alkyl group optionally having substituent(s)" include a $C_{1-7}$ alkyl group (e.g., a methyl, ethyl, propyl, isopropyl, butyl, isobutyl, sec-butyl, tert-butyl, pentyl, hexyl, heptyl group etc.). Examples of the "substituent" of the "alkyl group optionally having substituent(s)" include a halogen atom, a hydroxy group, a $C_{1-6}$ alkoxy group (e.g., methoxy, ethoxy, propoxy, butoxy etc.), a $C_{1-6}$ alkoxy-carbonyl group (e.g., a methoxycarbonyl, ethoxycarbonyl, propoxycarbonyl group etc.), a carbamoyl group and the like. The number of the substituents may be 1 to 3. When the number of the substituents is not less than 2, respective substituents may be the same or different.

Examples of the "alkoxy group" of the "alkoxy group optionally having substituent(s)" include a $C_{1-6}$ alkoxy group (e.g., methoxy, ethoxy, propoxy, isopropoxy, butoxy, isobutoxy, pentoxy etc.) and the like. Examples of the "substituent" of the "alkoxy group optionally having substituent(s)" include those similar to the "substituent" of the above-mentioned "alkyl group optionally having substituent(s)". The number of the substituents is the same as in the above-mentioned "alkyl group optionally having substituent(s)".

Examples of the "aryl group" include a $C_{6-14}$ aryl group (e.g., a phenyl, 1-naphthyl, 2-naphthyl, biphenyl, 2-anthryl group etc.) and the like.

Examples of the "aryloxy group" include a $C_{6-14}$ aryloxy group (e.g., a phenyloxy, 1-naphthyloxy, 2-naphthyloxy group etc.) and the like.

Examples of the "acyl group" include a formyl, alkylcarbonyl, alkoxycarbonyl, carbamoyl, alkylcarbamoyl, alkylsulfinyl, alkylsulfonyl group and the like.

Examples of the "alkylcarbonyl group" include a $C_{1-6}$ alkyl-carbonyl group (e.g., an acetyl, propionyl group etc.) and the like.

Examples of the "alkoxycarbonyl group" include a $C_{1-6}$ alkoxy-carbonyl group (e.g., a methoxycarbonyl, ethoxycarbonyl, propoxycarbonyl, butoxycarbonyl group etc.) and the like.

Examples of the "alkylcarbamoyl group" include an N—$C_{1-6}$ alkyl-carbamoyl group (e.g., a methylcarbamoyl, ethylcarbamoyl group etc.), an N,N-di-$C_{1-6}$ alkyl-carbamoyl group (e.g., N,N-dimethylcarbamoyl, N,N-diethylcarbamoyl group etc.) and the like.

Examples of the "alkylsulfinyl group" include a $C_{1-7}$ alkylsulfinyl group (e.g., a methylsulfinyl, ethylsulfinyl, propylsulfinyl, isopropylsulfinyl group etc.) and the like.

Examples of the "alkylsulfonyl group" include a $C_{1-7}$ alkylsulfonyl group (e.g., a methylsulfonyl, ethylsulfonyl, propylsulfonyl, isopropylsulfonyl group etc.) and the like.

Examples of the "acyloxy group" include an alkylcarbonyloxy group, an alkoxycarbonyloxy group, a carbamoyloxy group, an alkylcarbamoyloxy group, an alkylsulfinyloxy group, an alkylsulfonyloxy group and the like.

Examples of the "alkylcarbonyloxy group" include a $C_{1-6}$ alkyl-carbonyloxy group (e.g., an acetyloxy, propionyloxy group etc.) and the like.

Examples of the "alkoxycarbonyloxy group" include a $C_{1-6}$ alkoxy-carbonyloxy group (e.g., a methoxycarbonyloxy, ethoxycarbonyloxy, propoxycarbonyloxy, butoxycarbonyloxy group etc.) and the like.

Examples of the "alkylcarbamoyloxy group" include a $C_{1-6}$ alkyl-carbamoyloxy group (e.g., a methylcarbamoyloxy, ethylcarbamoyloxy group etc.) and the like.

Examples of the "alkylsulfinyloxy group" include a $C_{1-7}$ alkylsulfinyloxy group (e.g., methylsulfinyloxy, ethylsulfinyloxy, propylsulfinyloxy, isopropylsulfinyloxy group etc.) and the like.

Examples of the "alkylsulfonyloxy group" include a $C_{1-7}$ alkylsulfonyloxy group (e.g., methylsulfonyloxy, ethylsulfonyloxy, propylsulfonyloxy, isopropylsulfonyloxy group etc.) and the like.

Examples of the "5- to 10-membered heterocyclic group" include a 5- to 10-membered (preferably 5- or 6-membered) heterocyclic group containing, besides carbon atoms, one or more (e.g., 1 to 3) heteroatoms selected from a nitrogen atom, a sulfur atom and an oxygen atom. Specific examples include a 2- or 3-thienyl group, a 2-, 3- or 4-pyridyl group, a 2- or 3-furyl group, a 1-, 2- or 3-pyrrolyl group, a 2-, 3-, 4-, 5- or 8-quinolyl group, a 1-, 3-, 4- or 5-isoquinolyl group, a 1-, 2- or 3-indolyl group and the like. Of these, a 5- or 6-membered heterocyclic group such as a 1-, 2- or 3-pyrrolyl group is preferable.

Ring A is preferably a benzene ring or a pyridine ring, each of which optionally has 1 or 2 substituents selected from a halogen atom, an optionally halogenated $C_{1-4}$ alkyl group, an optionally halogenated $C_{1-4}$ alkoxy group and 5- or 6-membered heterocyclic group.

Examples of the "aralkyl group" of the "aralkyl group optionally having substituent(s)" for $R^1$ include a $C_{7-16}$ aralkyl group (e.g., a $C_{6-10}$ aryl-$C_{1-6}$ alkyl group such as benzyl, phenethyl etc.) and the like. Examples of the "substituent" of the "aralkyl group optionally having substituent(s)" include those similar to the "substituent" of the above-mentioned "alkyl group optionally having substituent(s)". The number of the substituents is 1 to 4. When the number of the substituents is not less than 2, respective substituents may be the same or different.

Examples of the "acyl group" for $R^1$ include those similar to the "acyl group" exemplified as the substituent of the above-mentioned ring A.

Examples of the "acyloxy group" for $R^1$ include those similar to the "acyloxy group" exemplified as the substituent of the above-mentioned ring A.

$R^1$ is preferably a hydrogen atom.

Examples of the "alkyl group optionally having substituent(s)" for $R^2$, $R^3$ or $R^4$ include those similar to the "alkyl group optionally having substituent(s)" exemplified as the substituent of the above-mentioned ring A.

Examples of the "alkoxy group optionally having substituent(s)" for $R^2$, $R^3$ or $R^4$ include those similar to the "alkoxy group optionally having substituent(s)" exemplified as the substituent of the above-mentioned ring A.

Examples of the "amino group optionally having substituent(s)" for $R^2$, $R^3$ or $R^4$ include an amino group, a mono-$C_{1-6}$ alkylamino group (e.g., methylamino, ethylamino etc.), a mono-$C_{6-14}$ arylamino group (e.g., phenylamino, 1-naphthylamino, 2-naphthylamino etc.), a di-$C_{1-6}$ alkylamino group (e.g., dimethylamino, diethylamino etc.), a di-$C_{6-14}$ arylamino group (e.g., diphenylamino etc.) and the like.

$R^2$ is preferably a $C_{1-6}$ alkyl group, a $C_{1-6}$ alkoxy group, a $C_{1-6}$ alkoxy-$C_{1-6}$ alkoxy group or a di-$C_{1-6}$ alkylamino group. $R^2$ is more preferably a $C_{1-3}$ alkyl group or a $C_{1-3}$ alkoxy group.

$R^3$ is preferably a hydrogen atom, a $C_{1-6}$ alkoxy-$C_{1-6}$ alkoxy group or an optionally halogenated $C_{1-6}$ alkoxy group. $R^3$ is more preferably a $C_{1-3}$ alkoxy group which is halogenated or optionally substituted by a $C_{1-3}$ alkoxy group.

$R^4$ is preferably a hydrogen atom or a $C_{1-6}$ alkyl group. $R^4$ is more preferably a hydrogen atom or a $C_{1-3}$ alkyl group (it is particularly preferably a hydrogen atom).

Specific examples of the compound represented by the formula (I) include 2-[[[3-methyl-4-(2,2,2-trifluoroethoxy)-2-pyridinyl]methyl]sulfinyl]-1H-benzimidazole, 2-[[(3,5-dimethyl-4-methoxy-2-pyridinyl)methyl]sulfinyl]-5-methoxy-1H-benzimidazole, 2-[[[4-(3-methoxypropoxy)-3-methyl-2-pyridinyl]methyl]sulfinyl]-1H-benzimidazole sodium salt, 5-difluoromethoxy-2-[[(3,4-dimethoxy-2-pyridinyl)methyl]sulfinyl]-1H-benzimidazole, 2-[(RS)-[(4-methoxy-3-methylpyridin-2-yl)methyl]sulfinyl]-5-(1H-pyrrol-1-yl)-1H-benzimidazole and the like.

In the present invention, more specifically, benzimidazole compounds such as lansoprazole, omeprazole, S-omeprazole, pantoprazole, rabeprazole, tenatoprazole, ilaprazole and the like and imidazopyridine compounds are preferably used as the compound represented by the formula (I) which is the proton pump inhibitor.

Of these compounds, lansoprazole, i.e., 2-[[[3-methyl-4-(2,2,2-trifluoroethoxy)-2-pyridinyl]methyl]sulfinyl]-1H-benzimidazole is particularly preferable.

The aforementioned compound (I) may be a racemate or an optically active form such as R-form, S-form. For example, it may be an optically active form of lansoprazole, i.e. R-form or S-form of lansoprazole, and the like. It is particularly preferable an optically active form such as (R)-2-[[[3-methyl-4-(2,2,2-trifluoroethoxy)-2-pyridinyl]methyl]sulfinyl]-1H-benzimidazole and the like.

In the present invention, the proton pump inhibitor may be a pharmaceutically acceptable salt of the compound represented by the formula (I) or an optically active form thereof. The salt is preferably a pharmaceutically acceptable salt. Examples thereof include salts with inorganic base, salts with organic base, salts with basic amino acid, and the like.

Preferable examples of the salt with inorganic base include alkali metal salts such as sodium salt, potassium salt and the like; alkaline earth metal salts such as calcium salt, magnesium salt and the like; ammonium salt and the like.

Preferable examples of the salt with organic base include salts with alkylamines (trimethylamine, triethylamine etc.), heterocyclic amines (pyridine, picoline etc.), alkanol amines (ethanolamine, diethanolamine, triethanolamine etc.), dicyclohexylamine, N,N'-dibenzylethylenediamine and the like.

Preferable examples of the salt with basic amino acid include salts with arginine, lysine, ornithine and the like.

Of these salts, alkali metal salts and alkaline earth metal salts are preferable. Sodium salt is particularly preferable.

The compound represented by the formula (I) can be produced according to a method known per se, for example, the method described in JP-A-61-50978, U.S. Pat. No. 4,628,098, JP-A-10-195068, WO 98/21201 or the like or a method analogous thereto. In addition, the optically active compound represented by the formula (I) can be produced according to a method such as optical resolution (fractional recrystallization, chiral column method, diastereomer method, a method using microorganism or enzyme, and the like), asymmetric oxidation and the like. For example, R form lansoprazole can also be produced according to the method described in WO 00/78745, WO 01/83473, WO 01/87874 and WO 02/44167.

The orally-disintegrating solid preparation of the present invention may contain two or more (preferably 2 or 3) kinds of the above-mentioned pharmaceutically active ingredients.

The pharmaceutically active ingredient may be diluted with a diluent and the like generally used in the fields of medicine, food and the like. In addition, the pharmaceutically active ingredient to be used may be treated for masking of a bitter taste.

The above-mentioned pharmaceutically active ingredient can be used, for example, in an amount of 0.01-50 parts by weight, more preferably 0.05-30 parts by weight, per 100 parts by weight of the solid preparation.

In the present invention, the "fine granules" is as defined in the Japanese Pharmacopoeia, the 15th edition (a powder wherein 10% or less of the total amount of the powder passes a 75 μm sieve). The mean particle size of the fine granules in the preparation of the present invention desirably has a mean particle size of about 500 μm or below, preferably about 400 μm or below, in order to prevent rough or powdery texture during administration of the orally-disintegrating solid preparation of the present invention. For example, it is about 100 μm-about 500 μm, preferably about 100 μm-about 400 μm.

Unless otherwise specified, the "mean particle size" means a volume median diameter (median diameter: a particle diameter corresponding to 50% of cumulative distribution). Examples include a laser diffraction particle size distribution measuring method, specifically, a method using a laser diffraction particle size distribution analyzer HEROS RODOS (manufactured by Sympatec, Germany).

One embodiment of the "fine granules" in the orally-disintegrating solid preparation of the present invention is fine granules showing controlled release of the pharmaceutically active ingredient, and the outermost layer of the fine granules is coated with a coating layer comprising HPMC and L-HPC.

Examples of the fine granules showing controlled release of a pharmaceutically active ingredient (hereinafter sometimes to be referred to as release control fine granules) include fine granules coated with a release-controlling film (enteric coating layer, diffusion control coating layer or a combination of these, etc.) on core granules comprising a pharmaceutically active ingredient, fine granules comprising a pharmaceutically active ingredient dispersed in a controlled release matrix and the like. The release of an active ingredient is controlled by coating fine granules comprising the active ingredient with a film capable of controlling release of the active ingredient, or dispersing the active ingredient in a controlled release matrix.

The fine granules showing controlled release of an active ingredient also include fine granules coated with a general enteric film that dissolves at about pH 5.5. That is, examples of the release-controlling film include a general enteric film that dissolves at about pH 5.5, as well as films having a more superior release-delaying function or a release-sustaining function of an active ingredient such as a film that dissolves at a higher pH region and a pH-dependent manner, or a diffusion control coating layer wherein the film itself is not dissolved but an active ingredient is released through the film itself or fine pores formed in the film and the like.

The film in the controlled release film includes not only a film-like coating layer but also a coating layer having a greater thickness, and further, not only a coating layer that completely covers core granules or layers inside, but also a coating layer that covers most of the core granules or layers inside, though partially not covering them. The coating layer that covers most of the core granules or layers inside preferably covers at least 80% or more of the surface of the core granules or the layers inside, preferably the entirety thereof.

In a particularly preferable embodiment of the fine granules showing controlled release of a pharmaceutically active ingredient, fine granules comprising the core granule composed of at least one pharmaceutically active ingredient is coated with a release-controlling film are included.

Such core granule is obtained by coating an inactive carrier as a core with a pharmaceutically active ingredient, or by granulation using a pharmaceutically active ingredient and excipient generally used for preparation making. For example, it can be produced by the method described in JP-A-63-301816.

The mean particle size of the "core" may be about 40 to about 350 μm, preferably about 50 to about 250 μm, more preferably 100 to 250 μm, particularly preferably about 100 to about 200 μm. The cores having the above-described mean particle size include particles all of which pass through a No. 50 (300 μm) sieve, about 5 w/w % or less of the entirety of which remains on a No. 60 (250 m) sieve, and about 10 w/w % or less of the entirety of which passes through a No. 282 (53 μm) sieve. The specific volume of the "core" is 5 ml/g or less, preferably 4 ml/g or less, more preferably 3 ml/g or less.

Examples of the inactive carrier to be used as the "core" include (1) a spherical granulated product of crystalline cellulose and lactose, (2) a spherical crystalline cellulose having a size of 75 to 300 μm (CELPHERE, manufactured by Asahi Kasei Corporation), (3) a granule having a size of 50 to 250 μm produced from lactose (9 parts) and α-starch (1 part) by stirring granulation, (4) a micro particle having a size of 250 μm or smaller obtained by classification of microcrystalline cellulose spherical granules described in JP-A 61-213201, (5) a processed product of wax which is formed into a sphere by spray chilling or melt granulation, (6) a processed product such as a gelatin bead comprising an oil ingredient, (7) calcium silicate, (8) starch, (9) a porous particle such as chitin, cellulose, chitosan or the like, (10) a bulk powder of granulated sugar, crystalline lactose, crystalline cellulose, sodium chloride or the like, and a processed preparation thereof. Further, these cores may be produced by a per se known grinding method or granulation method, and then sieved to prepare particles having the desired particle diameter.

Examples of the "spherical granulated product of crystalline cellulose and lactose" include (i) a spherical granule having a size of 100 to 200 μm produced from crystalline cellulose (3 parts) and lactose (7 parts) (e.g., Nonpareil 105 (70-140) (particle diameter: 100 to 200 μm), manufactured by Freund Corporation), (ii) a spherical granule having a size of 150 to 250 μm produced from crystalline cellulose (3 parts) and lactose (7 parts) (e.g., Nonpareil NP-7:3, manufactured by Freund Corporation), (iii) a spherical granule having a size of 100 to 200 μm produced from crystalline cellulose (4.5 parts) and lactose (5.5 parts) (e.g., Nonpareil 105T (70-140) (particle diameter: 100 to 200 μm), manufactured by Freund Corporation), (iv) a spherical granule having a size of 150 to 250 μm produced from crystalline cellulose (5 parts) and lactose (5 parts) (e.g., Nonpareil NP-5:5, manufactured by Freund Corporation) and the like.

In order to produce a preparation retaining a suitable strength and having excellent solubility, the "core" is preferably a spherical granule of crystalline cellulose and lactose, and more preferably a spherical granule of crystalline cellulose and lactose which contains 50% by weight or more of lactose. A spherical granule composed of about 20-about 50 wt %, preferably about 40-about 50 wt %, of crystalline cellulose and about 50-about 80 wt %, preferably about 50-about 60 wt %, of lactose is also preferable.

Examples of the "spherical crystalline cellulose" include CELPHERE (CP-203 (particle size 150-300 μm), CP-102 (particle size 106-212 μm), SCP-100 (particle size 75-212 μm), manufactured by Asahi Kasei Chemicals Co., Ltd.) and the like.

As the core to be used in the present invention, spherical crystalline cellulose or a spherical granule of crystalline cellulose and lactose is preferable, and a 100-200 μm spherical granule of 100-250 μm of spherical crystalline cellulose or crystalline cellulose (4.5 parts) and lactose (5.5 parts) is more preferable.

When core granules are obtained by coating a pharmaceutically active ingredient on the core of an inactive carrier, as in the below-mentioned (1) fine granules having an enteric coating layer on core granules, and (2) fine granules having a diffusion control coating layer on core granules, or fine granules having an enteric coating layer and a diffusion control coating layer in combination on core granules and the like, for example, the core granules comprising the active ingredient can be prepared by wet granulation using a centrifugal fluid bed granulator (CF-mini, CF-360, manufactured by Freund Corporation) or a rotary bed granulator (MP-10, manufactured by POWREX Corporation) and the like. Alternatively, a pharmaceutically active ingredient may be sprayed for coating on while adding a spray solution comprising a binder and the like on the core of an inactive carrier, and the like. While the production apparatus is not limited, for example, a centrifugal fluid bed granulator and the like are preferably used for production by the latter coating. The coating using the aforementioned two kinds of apparatuses may be combined to apply an active ingredient in two steps. When the core of an inactive carrier is not used, core granules are obtained by the use of an excipient such as lactose, sucrose, mannitol, cornstarch, crystalline cellulose and the like and an active ingredient, a binder such as HPMC, hydroxypropyl cellulose, methylcellulose, polyvinyl alcohol, macrogol, pluronic F68, gum arabic, gelatin, starch and the like, and adding, where necessary, a disintegrant such as carboxymethylcellulose sodium, calcium carboxymethylcellulose, croscarboxymethylcellulose sodium (Ac-Di-Sol, manufactured by FMC International), polyvinylpyrrolidone, L-HPC and the like in a high-shear granulator, a wet extrusion-granulator, a fluid bed granulator and the like.

In the present invention, a basic inorganic salt is preferably added to granules, specifically, core granules comprising a pharmaceutically active ingredient, so as to stabilize the pharmaceutically active ingredient (particularly, a pharmaceutically active ingredient unstable to acid) in a preparation. The basic inorganic salt is preferably contacted with a pharmaceutically active ingredient, and preferably uniformly mixed with an active ingredient.

Examples of the "basic inorganic salt" include basic inorganic salts of sodium, potassium, magnesium and/or calcium (e.g., sodium carbonate, sodium hydrogen carbonate, potassium carbonate, potassium hydrogen carbonate, heavy magnesium carbonate, magnesium carbonate, magnesium oxide, magnesium hydroxide and the like).

The amount of the basic inorganic salt to be used is appropriately determined according to the kind of the basic inorganic salt, and, for example, 0.3-200 wt %, preferably 1-100 wt %, more preferably 10-50 wt %, most preferably 20-40 wt %, of the pharmaceutically active ingredient.

Core granulates comprising an active ingredient may be coated to form an intermediate coating layer before applying the below-mentioned release-controlling film. When the main drug is, for example, a pharmaceutically active ingredient unstable to acid such as PPI, etc. and the like, shutting off the direct contact between the core granules containing the active ingredient and the release-controlling film by forming an intermediate coating layer is preferable for improving the stability of the drug. Such an intermediate coating layer may be formed with a plurality of layers.

Examples of the coating substance for an intermediate coating layer include a polymer base such as L-HPC, hydroxypropyl cellulose, HPMC (e.g., TC-5 etc.), polyvinylpyrrolidone, polyvinyl alcohol, methylcellulose, hydroxyethylmethylcellulose and the like, which are appropriately added with sucrose [purified sucrose (pulverized (powder sugar), non-pulverized) etc.], starch sugar such as cornstarch and the like, saccharides such as lactose, honey and sugar alcohol (D-mannitol, erythritol and the like) and the like, and the like. Preferred are L-HPC, HPMC, D-mannitol, and a mixture of these. The intermediate coating layer may appropriately contain, besides these, an excipient (e.g., masking agent (titanium oxide etc.), an antistatic agent (titanium oxide, talc etc.)) added, where necessary, for the below-mentioned production of a preparation.

The amount of the intermediate coating layer to be applied is generally about 0.02 part by weight-about 1.5 parts by weight, preferably about 0.05-about 1 part by weight, per 1 part by weight of the core granules (particles containing a main drug).

The coating can be performed according to a conventional method. For example, such intermediate coating layer components are preferably diluted with purified water and the like, and applied by spraying the liquid. In this case, a binder such as hydroxypropylcellulose and the like is preferably sprayed concurrently.

The fine granules showing controlled release of a pharmaceutically active ingredient and comprised in the orally-disintegrating solid preparation of the present invention are desirably fine granules having an enteric coating layer and/or a diffusion control coating layer on such core granules, or fine granules wherein an active ingredient is dispersed in a controlled release matrix.

In the release-controlling film of the present invention, an enteric coating layer and a diffusion control coating layer may be applied. Moreover, the release-controlling film of the present invention may comprise an enteric coating layer and a diffusion control coating layer in combination.

(1) Fine Granules Having Enteric Coating Layer on Core Granules

In a preferable embodiment of such fine granules, release-controlling film is formed on the aforementioned core granule, and fine granules having an enteric coating layer as the film are preferable. The enteric coating layer in the present invention comprises a coating substance which dissolves/elutes in a pH-dependent manner to control release, and the substance forms an enteric coating layer. Here, the "pH-dependent manner" means dissolution/elution in an environment with a pH of a given level or higher to release a pharmaceutically active ingredient.

In the preparation of the present invention, the enteric coating layer may be formed via the aforementioned intermediate coating layer formed on the core granules.

The enteric coating layer of the present invention contains a polymer such as hydroxypropylmethylcellulose phthalate (HP-55, HP-50, manufactured by Shin-Etsu Chemical Co., Ltd.), cellulose acetate phthalate, carboxymethylethylcellulose (CMEC, manufactured by Freund Corporation), methyl methacrylate-methacrylic acid copolymer (Eudragit L100 (methacrylic acid copolymer L) or Eudragit S100 (methacrylic acid copolymer S), manufactured by Rohm), methacrylic acid-ethyl acrylate copolymer (Eudragit L100-55 (dried methacrylic acid copolymer LD) or Eudragit L30D-55 (methacrylic acid copolymer LD), manufactured by Rohm), methacrylic acid-methyl acrylate-methyl methacrylate copolymer (Eudragit FS30D, manufactured by Rohm), hydroxypropylmethylcellulose acetate succinate (HPMCAS, manufactured by Shin-Etsu Chemical Co., Ltd.), polyvinyl acetatephthalate, shellac and the like as a coating substance to control release of the pharmaceutically active ingredient in a pH-dependent manner. Preferred are methyl methacrylate-methacrylic acid copolymer, methacrylic acid-methyl acrylate-methyl methacrylate copolymer and the like. Two or more (preferably 2-3) kinds of these coating substances may be used in combination.

In other words, the enteric coating layer of the present invention may have two or more kinds of coated films having different release conditions of the pharmaceutically active ingredient. Each coated film is a mixture of one or more kinds selected from the group consisting of hydroxypropylmethylcellulose phthalate, cellulose acetate phthalate, carboxymethylethylcellulose, methyl methacrylate-methacrylic acid copolymer, methacrylic acid-ethyl acrylate copolymer, methacrylic acid-methyl acrylate-methyl methacrylate copolymer, hydroxypropylmethylcellulose acetate succinate, polyvinyl acetatephthalate and shellac. Preferably, it is a mixture of one or more kinds selected from the group consisting of methyl methacrylate-methacrylic acid copolymer and methacrylic acid-methyl acrylate-methyl methacrylate copolymer.

Moreover, two or more kinds (preferably 2-3 kinds) of polymers as coating substances for the aforementioned enteric coating layer may be sequentially coated to form a multi-layer. To form two or more kinds of film that dissolve in different pH ranges, for example, a polymer that dissolves at not less than pH 6.0 and a polymer that dissolves at not less than pH 7.0 may be used in combination. For example, a polymer that dissolves at not less than pH 6.0 and a polymer that dissolves at not less than pH 7.0 may be used in combination at a ratio of 1:0.5-1:5.

Furthermore, the enteric coating layer in the present invention may contain, where necessary, plasticizer such as polyethylene glycol, dibutyl sebacate, diethyl phthalate, triacetin, triethyl citrate and the like, stabilizer, and the like. For example, when the plasticizer is triethyl citrate, the amount of the enteric coating layer decreases since the amount of triethyl citrate is increased, whereby the fine granules are downsized, thus realizing downsizing of the whole preparation. The amount of the coating substance used for release control is 5-200%, preferably 20-100%, more preferably 30-90%, relative to the core granules. The dissolution of the active ingredient from the thus-obtained fine granules showing controlled release of the active ingredient is desirably not more than 10% in 2 hr as expressed by the dissolution ratio of a pH 1.2 solution, and not more than 5% in 1 hr and not less than 60% in 8 hr as expressed by the dissolution ratio of a pH 6.8 solution.

The thus-obtained fine granules having a release-controlling film may be coated with a substance that becomes viscous on contact with water, such as polyethylene oxide (PEO, for example, Polyox WSR303 (molecular weight 7000000), Polyox WSR Coagulant (molecular weight 5000000), Polyox WSR 301 (molecular weight 4000000), Polyox WSR N-60K (molecular weight 2000000), Polyox WSR 205 (molecular weight 600000); manufactured by Dow Chemical), hydroxypropylmethylcellulose (HPMC, Metlose 90SH10000, Metlose 90SH50000, Metlose 90SH30000, manufactured by Shin-Etsu Chemical Co., Ltd.), carboxymethyl cellulose (CMC-Na, Sanlose F-1000MC), hydroxypropyl cellulose (HPC, for example, HPC-H, manufactured by Nippon Soda Co., Ltd.), hydroxyethyl cellulose (HEC), carboxyvinyl polymer (Hibiswako (R)103, 104, 105, manufactured by Wako Pure Chemical Industries, Ltd.; carbopol 943, manufactured by Goodrich), chitosan, sodium alginate, pectin and the like.

(2) Fine Granules Having Diffusion Control Coating Layer on Core Granules

The fine granules showing controlled release of an active ingredient are fine granules having a release-controlling film on the core granules comprising the active ingredient. As the film, fine granules having a diffusion control coating layer can be mentioned. The diffusion control coating layer in the present invention is a layer that controls release of a pharmaceutically active ingredient by diffusion. Such a diffusion control coating layer contains a diffusion control film-forming polymer. Examples of the diffusion control film-forming polymer include ethyl acrylate-methyl methacrylate-methacrylate trimethylammoniumethyl chloride copolymer (Eudragit RS (aminoalkylmethacrylate copolymer RS) and Eudragit RL (aminoalkylmethacrylate copolymer RL), manufactured by Rohm), methyl methacrylate-ethyl acrylate copolymer (Eudragit NE30D, manufactured by Rohm), ethylcellulose and the like. Preferably, ethyl acrylate-methyl methacrylate-trimethylammoniumethyl methacrylate chloride copolymer and methyl methacrylate-ethyl acrylate copolymer can be mentioned. These diffusion control film-forming polymers can also be used as a mixture of one or more kinds thereof.

Two or more kinds of diffusion control film-forming polymers in the diffusion control coating layer may be a mixture at a suitable ratio, and can also be used as a mixture with hydrophilic pore-forming substance such as HPMC, HPC, carboxyvinyl polymer, polyethylene glycol 6000, lactose, mannitol, organic acid and the like at a given ratio.

The release-controlling film in the present invention may be a film comprising an enteric coating layer and a diffusion control coating layer in combination. The fine granules showing controlled release of a pharmaceutically active ingredient may be coated with a release-controlling film comprising the aforementioned diffusion control coating layer and the enteric coating layer of the aforementioned (1) in combination. Examples thereof include (i) a form wherein core granules comprising the active ingredient are coated with an enteric coating layer, and then a diffusion control coating layer, (ii) a form wherein core granules comprising the active ingredient are coated with a diffusion control coating layer, and then an enteric coating layer, and (iii) a form wherein core granules comprising the active ingredient are coated with a mixture of a coating substance to control release of a pharmaceutically active ingredient in a pH-dependent manner, which forms the aforementioned enteric coating layer, and the aforementioned diffusion control film-forming polymer to form a diffusion control coating layer and the like.

The coating layers of the aforementioned (i) and (ii) may be form a multi-layer as necessary. The coating substance to control release of a pharmaceutically active ingredient in a pH-dependent manner, and the diffusion control film-forming polymer of the aforementioned (iii) may be uniformly mixed or partly nonuniform. The mixing ratio of the mixture of a coating substance to control release of a pharmaceutically active ingredient in a pH-dependent manner and the diffusion control film-forming polymer is 1:10-10:1, more preferably 1:5-10:1, still more preferably 1:1-9:1.

To provide fine granules which release an active ingredient after a given lag time, a swellable substance such as disintegrant and the like may be coated before coating the aforementioned diffusion control coating layer so as to form a disintegrant layer between the core granules comprising the active ingredient and the release-controlling film. For example, a swellable substance such as croscarmellose sodium (Ac-Di-Sol, manufactured by FMC International), carmellose calcium (ECG505, manufactured by Gotoku Yakuhin), crospovidone (ISP Inc), low-substituted hydroxypropyl cellulose (L-HPC, manufactured by Shin-Etsu Chemical Co., Ltd.) and the like may be primarily applied onto the core granules comprising an active ingredient, and ethyl acrylate-methyl methacrylate-trimethylammoniumethyl methacrylate chloride copolymer (Eudragit RS or Eudragit RL, manufactured by Rohm), methyl methacrylate-ethyl acrylate copolymer (Eudragit NE30D, manufactured by Rohm), ethylcellulose and the like alone or in a mixture, or a diffusion control film obtained by mixing with a hydrophilic pore-forming substance such as HPMC, HPC, carboxyvinyl polymer, polyethylene glycol 6000, lactose, mannitol, organic acid and the like at a given ratio is preferably coated secondarily.

Such coating substance for secondary coating may be an enteric polymer that releases an active ingredient in a pH-dependent manner such as hydroxypropylmethylcellulose phthalate (HP-55, HP-50, manufactured by Shin-Etsu Chemical Co., Ltd.), cellulose acetate phthalate, carboxymethylethylcellulose (CMEC, manufactured by Freund Corporation), methyl methacrylate-methacrylate copolymer (Eudragit L100 (methacrylate copolymer L) or Eudragit S100 (methacrylate copolymer S), manufactured by Rohm), methacrylate-ethyl acrylate copolymer (Eudragit L100-55 (dried methacrylate copolymer LD) or Eudragit L30D-55 (methacrylate copolymer LD), manufactured by Rohm), methacrylate-methyl acrylate-methyl methacrylate copolymer (Eudragit FS30D, manufactured by Rohm), hydroxypropylmethylcellulose acetate succinate (HPMCAS manufactured by Shin-Etsu Chemical Co., Ltd.), polyvinyl acetate phthalate, shellac and the like.

The amount of the coating substance used for release control by diffusion control is desirably 1-200%, preferably 2-100%, more preferably 5-60%, relative to the core granules.

The coating may contain, where necessary, a plasticizer such as polyethylene glycol, dibutyl sebacate, diethyl phthalate, triacetin, triethyl citrate and the like, a stabilizer and the like. The thus-obtained fine granules showing controlled release of an active ingredient may be coated with a substance that becomes viscous on contact with water, such as polyethylene oxide (PEO, for example, Polyox WSR303 (molecular weight 7000000), Polyox WSR Coagulant (molecular weight 5000000), Polyox WSR 301 (molecular weight 4000000), Polyox WSR N-60K (molecular weight 2000000), Polyox WSR 205 (molecular weight 600000); manufactured by Dow Chemical), hydroxypropylmethylcellulose (HPMC, Metlose 90SH10000, Metlose 90SH50000, Metlose 90SH30000, manufactured by Shin-Etsu Chemical Co., Ltd.), carboxymethylcellulose (CMC-Na, Sanlose F-1000MC), hydroxypropylcellulose (HPC, for example, HPC-H, manufactured by Nippon Soda Co., Ltd.), hydroxyethylcellulose (HEC), carboxyvinyl polymer (Hibiswako (R)103, 104, 105, manufactured by Wako Pure Chemical Industries, Ltd.; carbopol 943, manufactured by Goodrich), chitosan, sodium alginate, pectin and the like, and the resulting fine granules may be used as controlled release fine granules.

When the aforementioned (1) fine granules having enteric coating layer on core granules and (2) fine granules having a diffusion control coating layer on the core granules are fine granules having two or more kinds of release-controlling films with different release conditions of the active ingredient, a layer comprising an active ingredient may be formed between the release-controlling films. An embodiment of the multi-layer structure comprising an active ingredient between the release-controlling films includes fine granules obtained by coating fine granules showing controlled release of a pharmaceutically active ingredient due to the release-controlling film with an active ingredient and then with the aforementioned release-controlling film.

(3) Fine Granules with Pharmaceutically Active Ingredient Dispersed in Release Control Matrix Another form of the fine granules showing controlled release of a pharmaceutically active ingredient includes fine granules with an active ingredient dispersed in a release control matrix. Such controlled release fine granules can be produced by uniformly dispersing an active ingredient in wax such as hydrogenated castor oil, hydrogenated rapeseed oil, stearic acid, stearyl alcohol and the like, or a hydrophobicity carrier such as polyglycerin fatty acid ester and the like. The matrix is a composition wherein an active ingredient is uniformly dispersed in a carrier and, where necessary, an excipient such as lactose, mannitol, cornstarch, crystalline cellulose and the like, generally used for formulation of preparations, may be dispersed together with the pharmaceutically active ingredient. Furthermore, a powder that produces viscose gel upon contact with water, such as polyoxyethyleneoxide, crosslinking type acrylic acid polymer (Hibiswako (R)103, 104, 105, carbopol), HPMC, HPC, chitosan and the like may be dispersed in the matrix together with an active ingredient and an excipient.

For preparation, a method known per se such as spray drying, spray chilling, melt granulation and the like can be employed.

The thus-obtained fine granules showing controlled release of an active ingredient may be coated with a substance that becomes viscous upon contact with water, such as polyethylene oxide polyethylene oxide (PEO, for example, Polyox WSR303 (molecular weight 7000000), Polyox WSR Coagulant (molecular weight 5000000), Polyox WSR 301 (molecular weight 4000000), Polyox WSR N-60K (molecular weight 2000000), Polyox WSR 205 (molecular weight 600000); manufactured by Dow Chemical), hydroxypropylmethylcellulose (HPMC, Metlose 90SH10000, Metlose 90SH50000, Metlose 90SH30000, manufactured by Shin-Etsu Chemical Co., Ltd.), carboxymethyl cellulose (CMC-Na, Sanlose F-1000MC), hydroxypropylcellulose (HPC, for example, HPC-H, manufactured by Nippon Soda Co., Ltd.), hydroxyethylcellulose (HEC), carboxyvinyl polymer (Hibiswako (R)103, 104, 105, manufactured by Wako Pure Chemical Industries, Ltd.; carbopol 943, manufactured by Goodrich), chitosan, sodium alginate, pectin and the like and the obtained fine granules may be used as controlled release fine granules.

The controlled release fine granules may have the aforementioned various release control films, a release control matrix and the like in combination.

After producing the fine granules showing controlled release of a pharmaceutically active ingredient as mentioned above, the outermost layer thereof is overcoated with a coating layer comprising hydroxypropylmethylcellulose (HPMC) and low-substituted hydroxypropylcellulose (L-HPC), whereby the "fine granules" capable of suppressing breakage of the fine granules during tableting can be obtained.

The "low-substituted hydroxypropylcellulose" means low-substituted hydroxypropylcellulose wherein the content of hydroxypropoxyl group in hydroxypropylcellulose (hereinafter sometimes to be abbreviated as HPC group content) is about 5.0-9.9 wt %. Particularly, it means low-substituted hydroxypropylcellulose of about 5.0-7.0 wt %, low-substituted hydroxypropylcellulose of about 7.0-9.9 wt % and the like.

Examples of the low-substituted hydroxypropylcellulose having an HPC group content of about 7.0-9.9 wt % include LH-22, LH-32, a mixture thereof and the like, which are available as commercially available products (Shin-Etsu Chemical Co., Ltd.). Also, they can also be produced by a method known per se, for example, the method described in JP-B-57-53100 or a method analogous thereto.

Examples of the low-substituted hydroxypropylcellulose having an HPC group content of about 5.0-7.0 wt % include LH-23, LH-33, a mixture thereof and the like. These can be produced by a method known per se, for example, the method described in JP-B-57-53100 or a method analogous thereto.

The particle size of the "low-substituted hydroxypropylcellulose having a hydroxypropoxyl group content of 5.0-7.0 wt %" is, for example, about 5-60 µm, preferably about 7-50 µm, more preferably about 10-40 µm, as an average particle size.

Using L-HPC having a relatively large particle size (for example, L-HPC having an average particle size of about 26-40 µm) from among such ranges, a preparation superior in the disintegration property can be produced. On the other hand, using L-HPC having a relatively small particle size (for example, L-HPC having an average particle size of about 10-25 µm), a preparation superior in the preparation strength can be produced. Thus, the particle size of L-HPC can be appropriately selected according to the characteristic of the desired preparation.

Examples of HPMC include Hypromellose TC-5 (manufactured by Shin-Etsu Chemical Co., Ltd.) and the like.

In the present invention, the coating layer on the outermost layer preferably covers the entire surface of fine granules containing a pharmaceutically active ingredient in a layer thickness of 0.5-100 µm, preferably 1-50 µm, more preferably 2-30 µm. The coating amount of the coating layer comprising HPMC and L-HPC relative to the whole fine granules is 1-20 wt %, preferably 3-10 wt %. The coating layer on the outermost layer may contain, besides HPMC and L-HPC, an excipient (e.g., masking agents (titanium oxide etc.), antistatic agent (titanium oxide, talc etc.)) to be added as necessary to formulate preparations, and the like. However, the coating layer on the outermost layer preferably contains 9-91 wt % of HPMC and 9-91 wt % of L-HPC.

In the preparation of the present invention, the weight ratio of HPMC and L-HPC in the coating layer on the outermost layer of fine granules is 10:1-1:10, preferably 5:1-1:5.

The coating layer comprising HPMC and L-HPC can be applied by a method known per se using a stirring granulating machine, a fluid bed granulator and the like.

In an attempt to achieve a faster rise of blood concentration after oral administration, earlier efficacy expression, sustained therapeutically effective concentration for a long time, reduced administration frequency, an effective treatment with a small dose, and reduction of side effects caused by the rise of the blood concentration, the orally-disintegrating solid preparation of the present invention may contain two or more kinds (preferably 2-3 kinds) of fine granules with different release rates of the pharmaceutically active ingredient.

The size of the fine granules in the present invention is about 500 µm or below, preferably about 400 µm or below (e.g., about 100 µm-about 500 µm, preferably about 100 µm-about 400 µm). Using two or more kinds of fine granules with different release rates, a preparation controlling release of an active ingredient from fine granules continuously or in a pulse-like manner can also be designed. The fine granules with different release rates of a pharmaceutically active ingredient may contain the same pharmaceutically active ingredient, or contain a different pharmaceutically active ingredient in combination may be produced.

That is, the present invention provides an orally-disintegrating solid preparation comprising, in combination, (1) fine granules showing controlled release of a pharmaceutically active ingredient wherein the outermost layer of the fine granules is coated with a coating layer comprising HPMC and L-HPC, and (2) fine granules with a different release rate of a pharmaceutically active ingredient from that of the fine granules of (1).

Examples of the preparation of the present invention include an orally-disintegrating solid preparation comprising (1) fine granules A showing controlled release of a pharmaceutically active ingredient wherein the outermost layer of the fine granules is coated with a coating layer comprising HPMC and L-HPC, and (2) fine granules B with a different release rate of a pharmaceutically active ingredient from that of the fine granules of (1). While this preparation is explained in detail as one embodiment, the preparation is not limited thereto.

The fine granules A are the aforementioned fine granules showing controlled release of a pharmaceutically active ingredient, wherein the outermost layer of the fine granules is coated with a coating layer comprising HPMC and L-HPC.

In the above-mentioned preparation of the present invention, the pharmaceutically active ingredient in the fine granules A and the pharmaceutically active ingredient in the fine granules B may be the same or different, and they are preferably the same.

One example of fine granules B with a different release rate of a pharmaceutically active ingredient from that of granules A is shown in the following.

The mean particle size of the fine granules B in the present invention is about 500 µm or below, preferably about 400 µm or below (e.g., about 100 µm-about 500 µm, preferably about 100 µm-about 400 µm), in order to prevent rough or powdery texture during administration of the orally-disintegrating solid preparation of the present invention.

The pharmaceutically active ingredient in fine granules B is used in a proportion of, for example, 1-50 parts by weight, preferably 2-20 parts by weight, per 100 parts by weight of the fine granules B.

The weight ratio of the pharmaceutically active ingredient in the fine granules A and that in the fine granules B in the preparation of the present invention is 1:10-10:1.

When the pharmaceutically active ingredient is unstable to acid, such as PPI and the like, a basic inorganic salt is preferably added to stabilize the pharmaceutically active ingredient in the preparation. Examples of the basic inorganic salt include those similar to fine granules A.

The amount of the basic inorganic salt to be used is appropriately determined according to the kind of the basic inorganic salt, and is, for example, 0.3-200 wt %, preferably 1-100 wt %, more preferably 10-50 wt %, most preferably 20-40 wt %, relative to the pharmaceutically active ingredient.

The fine granules B may comprise a core with or without a pharmaceutically active ingredient. The core is similar to the inactive carrier that fine granules A may contain.

The core is coated with a pharmaceutically active ingredient and the like, and may be coated by a method known per se for the purpose of masking of taste and odor, enteric property or sustained release. Examples of the coating agent here include an aqueous enteric polymer material, such as hydroxypropylmethylcellulose phthalate, cellulose acetate phthalate, hydroxypropylmethylcellulose acetate succinate, methacrylate copolymer [for example, Eudragit L30D-55 (trade name; manufactured by Rohm), Kollicoat MAE30DP (trade name; manufactured by BASF), POLYQUID PA30 (trade name; manufactured by Sanyo Chemical Industry) and the like], carboxymethylethylcellulose, shellac and the like; sustained-release substance such as methacrylate copolymer [for example, Eudragit NE30D (trade name), Eudragit RL30D (trade name), Eudragit RS30D (trade name) and the like] and the like; water-soluble polymer; plasticizers such as triethyl citrate, polyethylene glycol, acetylation monoglyceride, triacetin, castor oil and the like, and the like. These can also be used as a mixture of one or more kinds thereof.

Specific examples of fine granules B in the present invention include a form wherein an enteric coating layer is formed on the core granules comprising the pharmaceutically active ingredient. The enteric coating layer in fine granules B in the present invention contains one or more kinds of aqueous enteric polymer materials selected from hydroxypropylmethylcellulose phthalate, cellulose acetate phthalate, hydroxypropylmethylcellulose acetate succinate, methacrylate copolymer, carboxymethylethylcellulose and shellac.

The enteric coating layer is preferably formed using an aqueous enteric polymer material and a sustained-release material and, where necessary, a plasticizer and the like in combination.

Preferable examples of the aqueous enteric polymer material include methacrylate-ethyl acrylate copolymer, hydroxypropylmethylcellulose acetate succinate and carboxymethylethylcellulose.

The enteric coating layer of the fine granules B in the present invention contains a polymer substance that dissolves within the range of generally not less than pH 5.0 and not more than pH 6.0.

The enteric coating layer of fine granules B in the present invention may contain a sustained-release material. Preferable examples of the sustained-release material include methacrylic acid copolymer such as methyl methacrylate-ethyl acrylate copolymer and the like, and ethylcellulose.

The amount of the above-mentioned sustained-release material to be used is about 5-30 wt %, preferably about 5-15 wt %, relative to 100 wt % of the aqueous enteric polymer material.

The fine granules B can also be produced by a known granulation method.

The "granulation method" includes, for example, rotary granulation method (e.g., centrifugal rolling granulation), fluidized-bed granulation (e.g., rotary fluidized bed granulation, fluidized granulation, etc.), stirring granulation and the like. Among others, preferred is fluidized-bed granulation method, more preferred is rotary fluidized-bed granulation method.

Concrete example of the rotary granulation method includes a method using "CF apparatus" manufactured by Freund Corporation and the like. Concrete examples of the rotary fluidized-bed granulation method include methods using "SPIR-A-FLOW", "multi plex" manufactured by Powrex Corporation, "New-Marumerizer" manufactured by Fuji Paudal Co., Ltd., and the like. The method for spraying the mixture can be suitably selected in accordance with the kind of granulator, and may be, for example, any one of a top spray method, a bottom spray method, a tangential spray method, and the like. Among others, a tangential spray method is preferred.

More specifically, for example, using the production method (coating method) described in JP-A-5-092918, and by a method of coating a core comprising crystalline cellulose and lactose with a pharmaceutically active ingredient (e.g., a pharmaceutically active ingredient unstable to acid) and, where necessary, a basic inorganic salt, a binder, a lubricant, an excipient, a water-soluble polymer and the like, core granules comprising the pharmaceutically active ingredient are obtained.

As the basic inorganic salt, binder, lubricant and excipient, those mentioned above and the like are used.

Examples of the "basic inorganic salt" include basic inorganic salts such as sodium, potassium, magnesium and/or calcium (e.g., sodium carbonate, sodium hydrogen carbonate, potassium carbonate, potassium hydrogen carbonate, heavy magnesium carbonate, magnesium carbonate, magnesium oxide, magnesium hydroxide, etc.) and the like.

Examples of the "binder" include hydroxypropylcellulose, HPMC, crystalline cellulose, starch, polyvinylpyrrolidone, gum arabic powder, gelatin, pullulan, L-HPC and the like.

Examples of the "lubricant" include magnesium stearate, sucrose fatty acid ester, polyethylene glycol, talc, stearic acid and the like.

Examples of the "excipient" include lactose, sucrose, D-mannitol, starch, cornstarch, crystalline cellulose, light anhydrous silicic acid, titanium oxide and the like.

Examples of the "water-soluble polymer" include ethanol soluble water-soluble polymer [for example, cellulose derivatives such as hydroxypropylcellulose and the like, polyvinylpyrrolidone and the like], ethanol-insoluble water-soluble polymer [for example, cellulose derivatives such as HPMC, methylcellulose, carboxymethylcellulose sodium and the like, sodium polyacrylate, polyvinyl alcohol, sodium alginate, guar gum and the like] and the like.

While the core may contain a pharmaceutically active ingredient, since a coating layer comprising a pharmaceutically active ingredient can control releaseability of the active ingredient, the core may not contain an active ingredient.

The core is preferably as uniformly spherical as possible so as to minimize variation of coating amount.

The proportion of the coating layer to the core can be selected from the range permitting control of the dissolution property of the pharmaceutically active ingredient and the granule size of the composition and is, for example, generally 50-400 parts by weight per 100 parts by weight of the core.

The coating layer may be formed by plurality layers. A combination of various coating layers, such as coating layer free of a pharmaceutically active ingredient, coating layer for base, enteric coating layer and the like, constituting the plural coating layers can be appropriately selected.

For coating of the core, for example, a mixture of the aforementioned pharmaceutically active ingredient and water-soluble polymer is used. The mixture may be a solution or a dispersion, which can be prepared using water or an organic solvent such as ethanol and the like, or a mixture thereof.

While the concentration of the water-soluble polymer in the mixture varies depending on the proportion of the pharmaceutically active ingredient and the additive, it is generally 0.1-50 wt %, preferably 0.5-10 wt %, so as to maintain the binding force of the pharmaceutically active ingredient to the core, as well as to maintain the viscosity of the mixture to prevent decreased workability.

When the coating layer comprises a plurality of layers, the concentration of the active ingredient in each layer may be changed successively or gradually by selecting the content of the water-soluble polymer or the viscosity grade of a mixture or by coating successively using mixtures which are different in the proportions of the pharmaceutically active ingredient and the other additives in the mixtures. In this case, coating may be performed using a mixture comprising the water-soluble polymer in an amount out of the range of 0.1 to 50% by weight, as long as coating layers in total contain 0.1 to 50% by weight of the water-soluble polymer. Further, the coating layer comprising a plurality of layers may comprise inert film layers formed by a known method so that the inert film layer can block each layer comprising the physiologically active substance.

When two or more kinds of pharmaceutically active ingredient which are incompatible are used, the core may be coated with each mixture of each pharmaceutically active ingredient together or separately.

After drying the above-mentioned coated product, a core granule composition with a uniform particle size through sieve can be obtained. The form of the composition generally corresponds to the core, and therefore, about spherical core granule composition can also be obtained. As the sieve, for example, a No. 50 (300 μm) round sieve can be used. By selecting the core granules that passed through the No. 50 round sieve, a core granule composition is obtained.

The aforementioned core granule composition is produced by coating a composition with an enteric coating layer for the purpose of protecting the pharmaceutically active ingredient or imparting enteric dissolution, in accordance with the same manner as the aforementioned granulation method. If necessary, the fine granule may be further coated with a water-soluble sugar alcohol (preferably mannitol). When coated with a water-soluble sugar alcohol, the strength of an orally-disintegrating tablet comprising the fine granules is improved.

The enteric coating layer comprises, for example, a combination of the aqueous enteric polymer base, the sustained-release base, the plasticizer and the like as described above, and is preferably a layer having a thickness of 20 to 70 μm, preferably 30 to 50 μm and coating the whole surface of a composition comprising the pharmaceutically active ingredient. Therefore, when the particle diameter of the composition is smaller, the weight percent of the enteric coating layer in the whole fine granules is higher. In the fine granules B of the present invention, the enteric coating layer is 30 to 70% by weight, preferably 50 to 70% by weight of the whole fine granules.

The enteric coating layer may be composed of a plurality of layers (e.g., 2 to 3 layers). An example of a coating method comprises coating a composition with an enteric coating layer comprising polyethylene glycol, with an enteric coating layer comprising triethyl citrate, and then with an enteric coating layer comprising polyethylene glycol.

The outermost layer of fine granules B may also be coated with a coating layer comprising HPMC and L-HPC, as in the case of fine granules A. The outermost layer can be coated with a coating layer comprising HPMC and L-HPC by a method similar to that for the aforementioned fine granules A.

The orally-disintegrating solid preparation (e.g. tablet) of the present invention can be produced in accordance with a conventional method in the pharmaceutical field.

Such methods include, for instance, a method which comprises blending the aforementioned fine granules (single fine granules, or 2-3 kinds of fine granules such as the aforementioned fine granules A and fine granules B and the like) and the "additives", and molding, if necessary followed by drying. Concretely mentioned is a method which comprises blending the fine granules and the additives, if necessary with water, and molding, if necessary followed by drying.

The "blending procedure" can be carried out by any of the conventional blending techniques such as admixing, kneading, granulating, etc. The above "blending procedure" is carried out, for instance, by using an apparatus such as Vertical granulator GV10 (manufactured by Powrex Corporation), Universal Kneader (manufactured by Hata Iron Works Co., Ltd.), fluidized bed coater LAB-1 and FD-3S (manufactured by Powrex Corporation), V-shape mixer, tumbling mixer, and the like.

A production method by wet tableting is preferably the method described in JP-A-5-271054 and the like. They may also be produced by drying after humidifying. The method is preferably the method described in JP-A-9-48726, JP-A-8-291051 and the like. That is, it is effective to enhance hardness by humidifying before or after tableting and drying thereafter.

When the solid preparation is a tablet, for example, "molding" can be performed by punching at a pressure of 0.5-3 ton/cm$^2$, preferably 1-2 ton/cm$^2$ and using a single punch tableting machine (manufactured by KIKUSUI SEISAKUSHO LTD.), rotary tableting machine (manufactured by KIKUSUI SEISAKUSHO LTD.) and the like.

The "drying" may be performed by any method generally used for drying preparations, such as vacuum drying, fluidized bed drying and the like.

As the additive to be blended with fine granules, for example, water-soluble sugar alcohol, crystalline cellulose or low-substituted hydroxypropylcellulose and the like can be used. The orally-disintegrating solid perpetration for oral administration can be produced by further adding and mixing a binder, an acidulant, an effervescent agent, an artificial sweetener, a flavor, a lubricant, a colorant, a stabilizing agent, an excipient, a disintegrant, and the like, and then compression molding the mixture. Alternatively, a dispersion of the pharmaceutically active ingredient in water can be placed in a mold (e.g., PTP molded pocket), dried with a lyophilizer or a circulation dryer, and then heat-sealed to obtain a molded tablet.

The term "water-soluble sugar alcohol" means a sugar alcohol which requires less than 30 ml of water for dissolution within about 30 minutes when 1 g of the sugar alcohol is added to water and then strongly shaken at 20° C. for 30 seconds every 5 minutes.

Examples of the "water-soluble sugar alcohol" include mannitol, sorbitol, maltitol, a hydrogenated starch hydrolysate, xylitol, reduced palatinose, erythritol, and the like. The water-soluble sugar alcohol may be a mixture of two or more kinds of them at an appropriate ratio.

The "water-soluble sugar alcohol" is preferably mannitol, xylitol or erythritol. Erythritol is conventionally produced by fermentation of glucose as a starting material with yeast or the like. Erythritol having a particle size of 50 mesh or less is used. The erythritol is commercially available (Nikken Chemicals Co., Ltd., etc.).

The amount of the water-soluble sugar alcohol is usually about 3 to 50 parts by weight, preferably about 5 to 30 parts by weight based on 100 parts by weight of a total preparation.

The "crystalline cellulose" may be obtained by partial depolymerization of α-cellulose followed by purification. The crystalline cellulose also includes that referred as microcrystalline cellulose. Specific examples of the crystalline cellulose include Ceolus KG 801, Ceolus KG 802, Avicel PH 101, Avicel PH 102, Avicel PH 301, Avicel PH 302, Avicel RC-591 (crystalline cellulose/carmellose sodium) and the like. Preferred is so-called high-compatible Avicel including Ceolus KG 801 and Ceolus KG 802. These crystalline celluloses may be used alone, or two or more kinds may be used in combination. These crystalline celluloses are commercially available (Asahi Kasei Corporation).

The crystalline cellulose may be incorporated in an amount of about 3 to 50 parts by weight, preferably about 5 to 40 parts by weight, most preferably about 5 to 20 parts by weight into 100 parts by weight of a total preparation.

The "low-substituted hydroxypropyl cellulose" is as mentioned above.

The L-HPC having an HPC group content of 5.0-7.0 wt % or 7.0-9.9 wt % to be used as an additive other than fine granules is added in a proportion of generally about 1-50 parts by weight, preferably about 1-40 parts by weight, more preferably about 1-20 parts by weight, per 100 parts by weight of the whole preparation, so as to afford sufficient disintegration property in the oral cavity and sufficient preparation strength.

Examples of the binder include hydroxypropyl cellulose, HPMC, crystalline cellulose, pregelatinized starch, polyvinylpyrrolidone, gum arabic powder, gelatin, pullulan, and the like. Two or more kinds of these binders may be used as a mixture at an appropriate ratio. When crystalline cellulose is used as the binder, a solid preparation retaining an excellent orally rapidly disintegrating property and having a higher strength can be obtained. The crystalline cellulose may be obtained by partial depolymerization of α-cellulose followed by purification. The crystalline cellulose also includes a cellulose referred to as microcrystalline cellulose. Specific examples of the crystalline cellulose include Ceolus KG 801, Ceolus KG 802, Avicel PH 101, Avicel PH 102, Avicel PH 301, Avicel PH 302, Avicel RC-A591NF (crystalline cellulose/carmellose sodium), Avicel RC-591 (crystalline cellulose/carmellose sodium) and the like. Preferred is so-called high-compatible crystalline cellulose including Ceolus KG 801 and Ceolus KG 802. These crystalline celluloses may be used alone, or two or more kinds may be used in combination. These crystalline celluloses are commercially available (Asahi Kasei Corporation). In the case of a solid preparation not comprising fine granules, the crystalline cellulose is used in an amount of for example, 1 to 50 parts by weight, preferably of 2 to 40 parts by weight, further preferably 2 to 20 parts by weight based on 100 parts by weight of the total preparation.

Examples of the acidulant include citric acid (anhydrous citric acid), tartaric acid, malic acid and the like.

Examples of the effervescent agent include sodium bicarbonate and the like.

Examples of the artificial sweetener include saccharine sodium, dipotassium glycyrrhizinate, aspartame, stevia, thaumatin and the like.

The flavor may be synthetic or natural, and examples thereof include lemon, lemon lime, orange, menthol, strawberry and the like.

Examples of the lubricant include magnesium stearate, a sucrose fatty acid ester, polyethylene glycol, talc, stearic acid and the like. When polyethylene glycol is used as the lubricant, a stable solid preparation in which degradation with time of a pharmaceutical ingredient is suppressed can be obtained. In this case, polyethylene glycol is used in an amount of for example, 0.01 to 10 parts by weight, preferably 0.1 to 5 parts by weight based on 100 parts by weight of the total preparation.

Examples of the colorant include edible dyes such as food Yellow No. 5, food Red No. 2, and food Blue No. 2; an edible lake dye, ferric oxide and the like.

Examples of the stabilizing agent include a basic substance in the case of a basic pharmaceutical ingredient, and an acidic substance in the case of an acidic pharmaceutical ingredient.

Examples of the excipient include lactose, white sugar, D-mannitol (β-D-mannitol, etc.), starch, corn starch, crystalline cellulose, light anhydrous silicic acid, titanium oxide and the like.

Examples of the disintegrant include so-called super disintegrants such as crospovidone [manufactured by ISP Inc. (USA), or BASF (Germany)], croscarmellose sodium (FMC-Asahi Kasei Corporation) and carmellose calcium (GOTOKU CHEMICAL COMPANY LTD.); hydroxypropyl cellulose, L-HPC; sodium carboxymethyl starch (Matsutani Chemical Industry Co., Ltd.); corn starch, and the like. Among them, crospovidone is preferably used. Two or more kinds of these disintegrants may be used as a mixture at an appropriate ratio.

The crospovidone may be any crosslinked polymer referred to as 1-ethenyl-2-pyrrolidinone homopolymer, including polyvinyl polypyrrolidone (PVPP) and 1-vinyl-2-pyrrolidinone homopolymers, and usually, the crospovidone having a molecular weight of 1,000,000 or more is used. Specific examples of commercially available crospovidone include cross-linked povidone, Kollidon CL [manufactured by BASF (Germany)], Polyplasdone XL, Polyplasdone XL-10, INF-10 [manufactured by ISP Inc. (USA)], polyvinylpyrrolidone, PVPP, 1-vinyl-2-pyrrolidinone homopolymers and the like.

These disintegrants may be used alone, or two or more kinds of them may be used in combination. For example, crospovidone may be used alone or in combination with other disintegrants.

The disintegrant is used in an amount of for example, 0.1 to 20 parts by weight, preferably 1 to 10 parts by weight, further preferably 3 to 7 parts by weight based on 100 parts by weight of a total preparation.

Starting material powders and granules may be punched at room temperature, or may be heat tableted at a temperature not lower than room temperature (about 25° C.-about 40° C.). In the present specification, the "room temperature" refers to the temperature in the room where tableting is performed in general tablet production, which is generally about 20° C.-about 25° C.

The solid preparation of the present invention comprises fine granules preferably having an average granule size of about 500 μm or below, and the solid preparation can be produced by punching fine granules having an average granule size of about 500 μm or below.

The dosage form of the orally-disintegrating solid preparation of the present invention is preferably a tablet (an orally-disintegrating tablet, a disintegrating tablet in water). Particularly preferred is an orally rapidly disintegrating tablet.

Tablets such as orally-disintegrating tablet and the like have a diameter of 6.5-20 mm, preferably 8-14 mm, to facilitate handling for administration.

In the case of a preparation comprising two or more kinds (preferably 2-3 kinds) of fine granules having different release rates of the pharmaceutically active ingredient, the contents of each fine granules and other additives are not particularly limited as long as the size thereof permits easy ingestion.

The orally-disintegrating solid preparation of the present invention comprising (1) fine granules A showing controlled release of a pharmaceutically active ingredient, which are coated with a coating layer comprising the outermost layer of HPMC and L-HPC, and (2) fine granules B with a different release rate of a pharmaceutically active ingredient from that of the fine granules B of (1) may further comprise an additive. In this case, a preparation comprising 10-50 wt % of fine granules A, 10-30 wt % of fine granules B and 20-80 wt % of an additive, relative to the whole preparation is preferable.

As the additive to be used for the aforementioned orally-disintegrating solid preparation comprising fine granules A and fine granules B, those mentioned above can be mentioned. Particularly, a water-soluble sugar alcohol, a disintegrant and the like are preferably used. The definition, specific examples, content and the like of the water-soluble sugar alcohol and disintegrant are mentioned above.

The total weight of the orally-disintegrating solid preparation of the present invention is not more than about 1000 mg, preferably 500-900 mg.

The oral disintegration time (a time until a solid preparation is completely disintegrated with saliva alone in the oral cavity of a healthy adult man or woman) of the preparation of the present invention is usually within about 90 seconds, preferably within 1 minute, more preferably 5 to 50 seconds, further preferably 5 to 40 seconds, particularly preferably 5 to 35 seconds.

The disintegration time in water of the preparation of the present invention is usually within about 90 seconds, preferably within 1 minute, more preferably 5 to 40 seconds, further preferably 5 to 30 seconds, particularly preferably 5 to 25 seconds.

The hardness (a value measured with a tablet hardness tester) of the preparation of the present invention is usually about 10 N to about 150 N (about 1 kg to about 15 kg).

The orally-disintegrating solid preparation of the present invention is administered without water or together with water. Examples of an administration method include (1) a method comprising holding the preparation of the present invention in the mouth and not swallowing the preparation as it is, and then dissolving or disintegrating the preparation with a small amount of water or with saliva in the oral cavity without water and (2) a method comprising swallowing a preparation as it is together with water. Alternatively, the tablet of the present invention may be dissolved or disintegrated with water, and then be administered.

A dose of the orally-disintegrating solid preparation (e.g., tablet) varies depending on a pharmaceutical ingredient, a subject to be administered, the kind of a disease and the like, and may be selected from such a range that the dose of a pharmaceutically active ingredient can be an effective amount.

For example, when the pharmaceutical ingredient is lansoprazole or optically active form thereof, the preparation of the present invention is useful for treatment and prevention of a peptic ulcer (e.g., stomach ulcer, duodenal ulcer, anastomomic ulcer, Zollinger-Ellinson syndrome, etc.), gastritis, erosive esophagitis, symptomatic Gastroesophageal Reflex Disease (symptomatic GERD) and the like; eradication or assistance in eradication of $H.$ $pylori$; suppression of upper gastrointestinal tract bleeding caused by peptic ulcer, acute stress ulcer or hemorrhagic gastritis; suppression of upper gastrointestinal tract bleeding caused by invasive stress (stress caused by major operation which requires central control after operation, or cerebrovascular disorder, head trauma, multiple organ failure or extensive burn which requires intensive care); treatment and prevention of an ulcer caused by a non-steroidal antiinflammatory agent; treatment and prevention of gastric hyperacidity and an ulcer caused by postoperative stress; administration before anesthesia and the like. The dose of the preparation is 0.5 to 1500 mg/day, preferably 5 to 500 mg/day, more preferably 5 to 150 mg/day per adult (60 kg body weight) of lansoprazole or optically active form thereof. Lansoprazole or an optically active form thereof may be used in combination with other pharmaceutical agents (antitumor agent, antibacterial agent etc.). Particularly, a combined use with an antibacterial agent selected from erythromycin antibiotics (e.g., clarithromycin etc.), penicillin antibiotics (e.g., amoxicillin etc.) and imidazole compounds (e.g., metronidazole etc.) affords a superior effect for eradication of $H.$ $pylori$.

When a PPI such as lansoprazole, an optically active form thereof and the like is used as a pharmaceutically active ingredient for the preparation of the present invention, a preparation capable of controlled release to achieve an average pH in the stomach at 0.5 hr after dosing of not less than 4, and pH 4 or above maintained for 14 hours or longer is desirable.

When the pharmaceutically active ingredient is voglibose, the preparation of the present invention is useful for the treatment and prophylaxis of obesity, adipositas, hyperlipemia, diabetes and the like, and the dose thereof is, as voglibose, 0.01-30 mg/day, preferably 0.01-10 mg/day, more preferably 0.1-3 mg/day, for an adult (60 kg body weight). The tablet may be administered once a day or in 2-3 portions a day.

The present invention provides a method of suppressing breakage of fine granules during tableting, which comprises coating the outermost layer of the fine granules in an orally-disintegrating tablet produced by tableting the fine granules showing controlled release of a pharmaceutically active ingredient and an additive, with a coating layer comprising hydroxypropylmethylcellulose (HPMC) and low-substituted hydroxypropylcellulose (L-HPC). According to this method, decreased masking effect of the bitter taste of the pharmaceutically active ingredient and decreased acid resistance due to the breakage of fine granules can be prevented.

The present invention is explained in more detail in the following by referring to Preparation Examples and Examples, which are not to be construed as limitative.

The components used in the following Examples and Comparative Examples were the Japanese Pharmacopoeia 15th Edition compatible products. Unless otherwise specified, % used hereafter means wt %. In the following Preparation Examples and Examples, compound X is (R)-2-[[[3-methyl-4-(2,2,2-trifluoroethoxy)-2-pyridinyl]methyl]sulfinyl]-1H-benzimidazole.

EXAMPLES

Preparation Example 1

Preparation of Core Granules

Core granules to be the core of controlled release fine granules A were produced as follows. Hydroxypropylmethyl cellulose (TC-SEW, 50 g) was dissolved in purified water (640 g), low-substituted hydroxypropyl cellulose (L-HPC-32W, 25 g) and magnesium carbonate (50 g) were dispersed in this solution. Compound X (150 g) was uniformly dispersed in the obtained dispersion to give a coating solution. The compound X-containing coating solution (793 g) was applied to lactose monohydrate-microcrystalline cellulose spheres (Nonpareil 105T, 130 g) with a rotary fluidized bed coater (SPIR-A-FLOW, manufactured by Freund Corporation). The coating conditions were: inlet temperature about 40° C., spray air pressure about 1 kgf/cm², exhaust air gauge 100, BED pressure about 250 mmHg, rotor speed about 300 rpm, spray rate about 6 g/min, spray gun position lower side. After the completion of coating, the obtained fine granules were dried in vacuo at 40° C. for 16 hr and passed through a round sieve to give core granules with a particle size of 125 μm-500 μm.

[Composition of Core Granules (85 mg)]

| lactose monohydrate-microcrystalline cellulose spheres (Nonpareil 105T) | 30 mg |
| compound X | 30 mg |
| magnesium carbonate | 10 mg |
| low-substituted hydroxypropylcellulose | 5 mg |
| hydroxypropylmethylcellulose | 10 mg |
| Total | 85 mg |

Preparation Example 2

Preparation of Intermediate Layer-Coated Fine Granules

The fine granules (core granules) obtained in Preparation Example 1 are coated with an intermediate layer coating solution using a rotary fluidized bed coater (SPIR-A-FLOW, manufactured by Freund Corporation), and directly dried to give fine granules having the following composition. The intermediate layer coating solution was produced by dissolving hydroxypropylmethylcellulose 2910 (16.8 g) and mannitol (16.8 g) in purified water (540 g), and dispersing titanium oxide (7.2 g), talc (7.2 g) and low-substituted hydroxypropylcellulose (L-HPC-32W, 12 g) in the obtained solution. The intermediate layer coating solution (500 g) was applied to the fine granules (170 g) obtained in Preparation Example 1 using a rotary fluidized bed coater (SPIR-A-FLOW, manufactured by Freund Corporation). The coating conditions were: inlet temperature about 60° C., spray air pressure about 1 kgf/cm², exhaust air gauge 100, BED pressure about 250 mmHg, rotor speed about 300 rpm, spray rate about 2.5 g/min, spray gun position lower side. After the completion of coating, the obtained fine granules were dried in vacuo at 40° C. for 16 hr and passed through a round sieve to give fine granules coated with intermediate layer with a particle size of 125 μm-500 μm.

[Composition in the Intermediate Layer-Coated Fine Granules (110 mg)]

| fine granules of Preparation Example 1 | 85 mg |
| hydroxypropylmethylcellulose 2910 | 7 mg |
| low-substituted hydroxypropylcellulose | 5 mg |
| talc | 3 mg |
| titanium oxide | 3 mg |
| mannitol | 7 mg |
| Total | 110 mg |

Preparation Example 3

Preparation of Enteric Fine Granules

Methacrylic acid copolymer S (108 g) and triethyl citrate (21.6 g) were dissolved in a mixed solution of purified water (165.2 g) and dehydrated ethanol (1487 g), and talc (54 g) was dispersed in the obtained solution to give a coating solution. The above-mentioned coating solution (1530 g) was applied to the fine granules (100 g) obtained in Preparation Example 2 using a rotary fluidized bed coater (SPIR-A-FLOW, manufactured by Freund Corporation). Using the coating conditions of inlet temperature about 35° C., spray air pressure about 1 kgf/cm², exhaust air gauge 100, BED pressure about 250 mmHg, rotor speed about 150 rpm, spray rate about 2.0 g/min and spray gun position lower side, a release-controlling film that dissolves in a pH-dependent manner (releases the active ingredient in a pH environment of a certain level or above) was formed. The obtained fine granules were dried in vacuo at 40° C. for 16 hr and passed through a round sieve to give enteric fine granules (125 μm-500 μm).

[Composition in Enteric Fine Granules (278.3 mg)]

| fine granules of Preparation Example 2 | 110 mg |
| methacrylic acid copolymer S | 99 mg |
| talc | 49.5 mg |
| triethyl citrate | 19.8 mg |
| Total | 278.3 mg |

Preparation Example 4

Preparation of the Outermost Layer-Coated Fine Granules

Hydroxypropylmethylcellulose 2910 (10.45 g) was dissolved in purified water (187.2 g), and low-substituted hydroxypropylcellulose (L-HPC-32W, 5.15 g) was dispersed in the obtained solution to give a coating solution. The above-mentioned coating solution (169 g) was applied to the fine granules (130 g) obtained in Preparation Example 3 using a rotary fluidized bed coater (SPIR-A-FLOW, manufactured by Freund Corporation). Using the coating conditions of inlet temperature about 40° C., spray air pressure about 1 kgf/cm$^2$, exhaust air gauge 100, BED pressure about 250 mmHg, rotor speed about 150 rpm, spray rate about 3.0 g/min and spray gun position lower side, the outermost layer coating layer was formed. The obtained fine granules were dried in vacuo at 40° C. for 16 hr and passed through a round sieve to give the outermost layer-coated fine granules (125 μm-500 μm).

[Composition in Outermost Layer-Coated Fine Granules (306.13 mg)]

| | |
|---|---|
| fine granules of Preparation Example 3 | 278.3 mg |
| hydroxypropylmethylcellulose 2910 | 18.55 mg |
| low-substituted hydroxypropylcellulose | 9.28 mg |
| Total | 306.13 mg |

Preparation Example 5

Preparation of Enteric Fine Granules

Methacrylic acid copolymer S (60 g) and triethyl citrate (12 g) were dissolved in a mixed solution of purified water (91.8 g) and dehydrated ethanol (826.2 g), and talc (30 g) was dispersed in the obtained solution to produce coating solution 1. Also, methacrylic acid copolymer S (60 g) and triethyl citrate (12 g) were dissolved in a mixed solution of purified water (91.8 g) and dehydrated ethanol (826.2 g), and magnesium stearate (30 g) was dispersed in the obtained solution to produce coating solution 2. The above-mentioned coating solution 1 (850 g) was applied to the fine granules (100 g) obtained in Preparation Example 2 with a rotary fluidized bed coater (SPIR-A-FLOW, manufactured by Freund Corporation) and, successively, the above-mentioned coating solution 2 (170 g) was applied with a rotary fluidized bed coater (SPIR-A-FLOW, manufactured by Freund Corporation). Using the coating conditions of inlet temperature about 35° C., spray air pressure about 1 kgf/cm$^2$, exhaust air gauge 100, BED pressure about 250 mmHg, rotor speed about 150 rpm, spray rate about 2.0 g/min and spray gun position lower side, a release-controlling film that dissolves in a pH-dependent manner (releases the active ingredient in a pH environment of a certain level or above) was formed. The obtained fine granules were dried in vacuo at 40° C. for 16 hr and passed through a round sieve to give enteric fine granules (125 μm-500 μm).

[Composition in Enteric Fine Granules (222.2 mg)]

| | |
|---|---|
| fine granules of Preparation Example 2 | 110 mg |
| methacrylic acid copolymer S | 66 mg |
| talc | 27.5 mg |
| magnesium stearate | 5.5 mg |
| triethyl citrate | 13.2 mg |
| Total | 222.2 mg |

Preparation Example 6

Preparation of Outermost Layer-Coated Fine Granules

Hydroxypropylmethylcellulose 2910 (10.45 g) was dissolved in purified water (187.2 g), and low-substituted hydroxypropylcellulose (L-HPC-32W, 5.15 g) was dispersed in the obtained solution to give a coating solution. The above-mentioned coating solution (169 g) was applied to the fine granules (130 g) obtained in Preparation Example 5 using a rotary fluidized bed coater (SPIR-A-FLOW, manufactured by Freund Corporation). Using the coating conditions of inlet temperature about 40° C., spray air pressure about 1 kgf/cm$^2$, exhaust air gauge 100, BED pressure about 250 mmHg, rotor speed about 150 rpm, spray rate about 3.0 g/min and spray gun position lower side, an outermost layer coating layer was formed. The obtained fine granules were dried in vacuo at 40° C. for 16 hr and passed through a round sieve to give the outermost layer-coated fine granules (125 μm-500 μm).

[Composition in Outermost Layer-Coated Fine Granules (244.42 mg)]

| | |
|---|---|
| fine granules of Preparation Example 5 | 222.2 mg |
| hydroxypropylmethylcellulose 2910 | 14.81 mg |
| low-substituted hydroxypropylcellulose | 7.41 mg |
| Total | 244.42 mg |

Preparation Example 7

Preparation of Core Granules

Core granules to be the core of controlled release fine granules A were prepared as follows. Hydroxypropylmethylcellulose (TC-SEW, 36 g) was dissolved in purified water (460.8 g), and low-substituted hydroxypropylcellulose (L-HPC-32W, 18 g) and magnesium carbonate (36 g) were dispersed in the solution. Compound X (108 g) was uniformly dispersed in the obtained dispersion to give a coating solution. The compound X-containing coating solution (565.6 g) was applied to microcrystalline cellulose spheres (CELPHERE CP203, 170 g) with a rotary fluidized bed coater (SPIR-A-FLOW, manufactured by Freund Corporation). The coating conditions were: inlet temperature about 40° C., spray air pressure about 1 kgf/cm$^2$, exhaust air gauge 100, BED pressure about 250 mmHg, rotor speed about 300 rpm, spray rate about 6 g/min and spray gun position lower side. After completion of the coating operation, the obtained fine granules were dried in vacuo at 40° C. for 16 hr and passed through a round sieve to give core granules with a particle size of 125 μm-500 μm.

[Composition in Core Granules (110 mg)]

| | |
|---|---|
| microcrystalline cellulose spheres (CELPHERE CP203) | 55 mg |
| compound X | 30 mg |
| magnesium carbonate | 10 mg |

| low-substituted hydroxypropylcellulose | 5 mg |
| hydroxypropylmethylcellulose | 10 mg |
| Total | 110 mg |

Preparation Example 8

Preparation of Intermediate Layer-Coated Fine Granules

An intermediate layer coating solution was applied to the fine granules (core granules) obtained in Preparation Example using a rotary fluidized bed coater (SPIR-A-FLOW, manufactured by Freund Corporation), and directly dried to give fine granules having the following composition. The intermediate layer coating solution was produced by dissolving hydroxypropylmethylcellulose 2910 (16.8 g) and mannitol (12 g) in purified water (496.8 g), and dispersing titanium oxide (7.2 g), talc (7.2 g) and low-substituted hydroxypropylcellulose (L-HPC-32W, 12 g) in the obtained solution. The intermediate layer coating solution (460 g) was applied to the fine granules (170 g) obtained in Preparation Example 7 using a rotary fluidized bed coater (SPIR-A-FLOW, manufactured by Freund Corporation). The coating conditions were: inlet temperature about 60° C., spray air pressure about 1 kgf/cm², exhaust air gauge 100, BED pressure about 250 mmHg, rotor speed about 300 rpm, spray rate about 2.5 g/min and spray gun position lower side. After completion of the coating operation, the obtained fine granules were dried in vacuo at 40° C. for 16 hr and passed through a round sieve to give intermediate layer-coated fine granules (125 μm-500 μm).

[Composition in Intermediate Layer-Coated Fine Granules (139.76 mg)]

| fine granules of Preparation Example 7 | 110 mg |
| hydroxypropylmethylcellulose 2910 | 9.06 mg |
| low-substituted hydroxypropylcellulose | 6.47 mg |
| talc | 3.88 mg |
| titanium oxide | 3.88 mg |
| mannitol | 6.47 mg |
| Total | 139.76 mg |

Preparation Example 9

Preparation of Controlled Release Fine Granules

Methacrylic acid copolymer S (42 g), aminoalkylmethacrylate copolymer RS (18 g) and triethyl citrate (18 g) were dissolved in a mixed solution of purified water (97.2 g) and dehydrated ethanol (874.8 g), and talc (30 g) was dispersed in the obtained solution to give a coating solution. The above-mentioned coating solution (900 g) was applied to the fine granules (100 g) obtained in Preparation Example 8 using a rotary fluidized bed coater (SPIR-A-FLOW, manufactured by Freund Corporation). Using the coating conditions of inlet temperature about 35° C., spray air pressure about 1 kgf/cm², exhaust air gauge 100, BED pressure about 250 mmHg, rotor speed about 150 rpm, spray rate about 2.0 g/min and spray gun position lower side, a controlled release film was formed. The obtained fine granules were dried in vacuo at 40° C. for 16 hr and passed through a round sieve to give controlled release fine granules (125 μm-500 μm).

[Composition in Controlled Release Fine Granules (215.23 mg)]

| fine granules of Preparation Example 8 | 139.76 mg |
| methacrylic acid copolymer S | 29.35 mg |
| aminoalkylmethacrylate copolymer RS | 12.58 mg |
| talc | 20.96 mg |
| triethyl citrate | 12.58 mg |
| Total | 215.23 mg |

Preparation Example 10

Preparation of Outermost Layer-Coated Fine Granules

Hydroxypropylmethylcellulose 2910 (10.45 g) was dissolved in purified water (187.2 g), and low-substituted hydroxypropylcellulose (L-HPC-32W, 5.15 g) was dispersed in the obtained solution to give a coating solution. The above-mentioned coating solution (169 g) was applied to the fine granules (130 g) obtained in Preparation Example 9 using a rotary fluidized bed coater (SPIR-A-FLOW, manufactured by Freund Corporation). Using the coating conditions of inlet temperature about 40° C., spray air pressure about 1 kgf/cm², exhaust air gauge 100, BED pressure about 250 mmHg, rotor speed about 150 rpm, spray rate about 3.0 g/min and spray gun position lower side, an outermost layer coating layer was formed. The obtained fine granules were dried in vacuo at 40° C. for 16 hr and passed through a round sieve to give the outermost layer-coated fine granules (125 μm-500 μm).

[Composition in Outermost Layer-Coated Fine Granules (236.76% mg)]

| fine granules of Preparation Example 9 | 215.24 mg |
| hydroxypropylmethylcellulose 2910 | 14.35 mg |
| low-substituted hydroxypropylcellulose | 7.17 mg |
| Total | 236.76 mg |

Preparation Example 11

Preparation of Core Granules

Core granules to be the core of controlled release fine granules B were prepared as follows. Hydroxypropylcellulose (HPC-L, 50 g) and mannitol (75 g) were dissolved in purified water (640 g), and low-substituted hydroxypropylcellulose (L-HPC-32W, 25 g) and magnesium carbonate (50 g) were dispersed in the solution. Compound X (75 g) was uniformly dispersed in the obtained dispersion to give a coating solution. The compound X-containing coating solution (793 g) was applied to lactose monohydrate-microcrystalline cellulose spheres (Nonpareil 105T, 130 g) with a rotary fluidized bed coater (SPIR-A-FLOW, manufactured by Freund Corporation). The coating conditions were: inlet temperature about 40° C., spray air pressure about 1 kgf/cm², exhaust air gauge 100, BED pressure about 250 mmHg, rotor speed about 300 rpm, spray rate about 6 g/min and spray gun position lower side. After completion of the coating operation, the obtained fine granules were dried in vacuo at 40° C. for 16 hr and passed through a round sieve to give core granules with a particle size of 125 μm-500 μm.

[Composition in Core Granules (85 mg)]

| lactose monohydrate-microcrystalline cellulose spheres (Nonpareil 105T) | 30 mg |
|---|---|
| compound X | 15 mg |
| mannitol | 15 mg |
| magnesium carbonate | 10 mg |
| low-substituted hydroxypropylcellulose | 5 mg |
| hydroxypropylcellulose | 10 mg |
| Total | 85 mg |

Preparation Example 12

Preparation of Intermediate Layer-Coated Fine Granules

An intermediate layer coating solution was applied to the fine granules (core granules) obtained in Preparation Example 11 using a rotary fluidized bed coater (SPIR-A-FLOW, manufactured by Freund Corporation), and directly dried to give fine granules having the following composition. The intermediate layer coating solution was produced by dissolving hydroxypropylmethylcellulose 2910 (16.8 g) and mannitol (16.8 g) in purified water (540 g), and dispersing titanium oxide (7.2 g), talc (7.2 g) and low-substituted hydroxypropylcellulose (L-HPC-32W, 12 g) in the obtained solution. The intermediate layer coating solution (500 g) was applied to the fine granules (170 g) obtained in Preparation Example 11 using a rotary fluidized bed coater (SPIR-A-FLOW, manufactured by Freund Corporation). The coating conditions were: inlet temperature about 60° C., spray air pressure about 1 kgf/cm², exhaust air gauge 100, BED pressure about 250 mmHg, rotor speed about 300 rpm, spray rate about 2.5 g/min and spray gun position lower side. After completion of the coating operation, the obtained fine granules were dried in vacuo at 40° C. for 16 hr and passed through a round sieve to give intermediate layer-coated fine granules (125 μm-500 μm).

[Composition in Intermediate Layer-Coated Fine Granules (110 mg)]

| fine granules of Preparation Example 11 | 85 mg |
|---|---|
| hydroxypropylmethylcellulose 2910 | 7 mg |
| low-substituted hydroxypropylcellulose | 5 mg |
| talc | 3 mg |
| titanium oxide | 3 mg |
| mannitol | 7 mg |
| Total | 110 mg |

Preparation Example 13

Preparation of Enteric Fine Granules

Glycerol monostearate (2.4 g), polysorbate 80 (0.72 g) and ferric oxide red (0.05 g) were added to purified water (73.7 g), and the mixture was heated in a homomixer (T. K. AUTOHOMOMIXER, manufactured by Tokushu Kika Kogyo) to 70° C., and cooled to room temperature to give a glycerol monostearate emulsion. Macrogol 6000 (4.08 g) and citric acid (0.05 g) were dissolved in purified water (50 g), and methacrylic acid copolymer LD (122.08 g) and ethyl acrylate-methyl methacrylate copolymer dispersion (13.6 g) were added. Glycerol monostearate emulsion was added to the obtained solution to give a coating solution. The above-mentioned coating solution (111.1 g) was applied to the fine granules (110 g) obtained in Preparation Example 12 using a rotary fluidized bed coater (SPIR-A-FLOW, manufactured by Freund Corporation). Using the coating conditions of inlet temperature about 35° C., spray air pressure about 1 kgf/cm², exhaust air gauge 100, BED pressure about 250 mmHg, rotor speed about 150 rpm, spray rate about 2.0 g/min and spray gun position lower side, a release-controlling film was formed. The obtained fine granules were dried in vacuo at 40° C. for 16 hr and passed through a round sieve to give enteric fine granules with a particle size of 125 μm-500 μm.

[Composition in Enteric Fine Granules (130 mg)]

| fine granules of Preparation Example 12 | 110 mg |
|---|---|
| methacrylic acid copolymer LD | 15.26 mg |
| ethyl acrylate-methyl methacrylate copolymer | 1.7 mg |
| macrogol 6000 | 1.7 mg |
| glycerol monostearate | 1.0 mg |
| polysorbate 80 | 0.3 mg |
| citric acid | 0.02 mg |
| ferric oxide red | 0.02 mg |
| Total | 130 mg |

Preparation Example 14

Preparation of Enteric Fine Granules

Glycerol monostearate (14.4 g), polysorbate 80 (4.32 g) and ferric oxide red (0.29 g) were added to purified water (470 g), and the mixture was heated in a homomixer (T. K. AUTOHOMOMIXER, manufactured by Tokushukika Co. Ltd.) to 70° C., and cooled to room temperature to give a glycerol monostearate emulsion. Triethyl citrate (44.88 g) and citric acid (0.12 g) were dissolved in purified water (319.4 g), and methacrylic acid copolymer LD (672 g) and ethyl acrylate-methyl methacrylate copolymer dispersion (74.64 g) were added. The glycerol monostearate emulsion was added to the obtained solution to give a coating solution. The above-mentioned coating solution (666.7 g) was applied to the fine granules (130 g) obtained in Preparation Example 13 using a rotary fluidized bed coater (SPIR-A-FLOW, manufactured by Freund Corporation). Using the coating conditions of inlet temperature about 35° C., spray air pressure about 1 kgf/cm², exhaust air gauge 100, BED pressure about 250 mmHg, rotor speed about 150 rpm, spray rate about 2.0 g/min and spray gun position lower side, a release-controlling film was formed. The obtained fine granules were dried in vacuo at 40° C. for 16 hr and passed through a round sieve to give enteric fine granules with a particle size of 125 μm-500 μm.

[Composition in Enteric Fine Granules (250 mg)]

| fine granules of Preparation Example 13 | 130 mg |
|---|---|
| methacrylic acid copolymer LD | 84 mg |
| ethyl acrylate-methyl methacrylate copolymer | 9.33 mg |
| triethyl citrate | 18.7 mg |
| glycerol monostearate | 6.0 mg |
| polysorbate 80 | 1.8 mg |
| citric acid | 0.05 mg |
| ferric oxide red | 0.12 mg |
| Total | 250 mg |

Preparation Example 15

Preparation of Enteric Fine Granules

Glycerol monostearate (1.2 g), polysorbate 80 (0.36 g) and ferric oxide red (0.02 g) were added to purified water (36.8 g), and the mixture was heated in a homomixer (T. K. AUTOHOMOMIXER, manufactured by Tokushukika Co. Ltd.) to 70° C., and cooled to room temperature to give a glycerol monostearate emulsion. Macrogol 6000 (2.04 g) and citric acid (0.02 g) were dissolved in purified water (25 g), and methacrylic acid copolymer LD (61.04 g) and ethyl acrylate-methyl methacrylate copolymer dispersion (6.8 g) were added. The glycerol monostearate emulsion was added to the obtained solution to give a coating solution. The above-mentioned coating solution (55.8 g) was applied to the fine granules (250 g) obtained in Preparation Example 14 using a rotary fluidized bed coater (SPIR-A-FLOW, manufactured by Freund Corporation). Using the coating conditions of inlet temperature about 35° C., spray air pressure about 1 kgf/cm$^2$, exhaust air gauge 100, BED pressure about 250 mmHg, rotor speed about 150 rpm, spray rate about 2.0 g/min and spray gun position lower side, a release-controlling film was formed. The obtained fine granules were dried in vacuo at 40° C. for 16 hr and passed through a round sieve to give enteric fine granules with a particle size of 125 μm-500 μm.

[Composition in Enteric Fine Granules (260 mg)]

| | |
|---|---|
| fine granules of Preparation Example 14 | 250 mg |
| methacrylic acid copolymer LD | 7.63 mg |
| ethyl acrylate-methyl methacrylate copolymer | 0.85 mg |
| macrogol 6000 | 0.85 mg |
| glycerol monostearate | 0.5 mg |
| polysorbate 80 | 0.15 mg |
| citric acid | 0.01 mg |
| ferric oxide red | 0.01 mg |
| Total | 260 mg |

Preparation Example 16

Preparation of Mannitol-Overcoated Enteric Fine Granules

Mannitol (24 g) was dissolved in purified water (216 g) to give a coating solution. The aforementioned coating solution (100 g) was applied to the fine granules (260 g) obtained in Preparation Example 15 using a rotary fluidized bed coater (SPIR-A-FLOW, manufactured by Freund Corporation). Using the coating conditions of inlet temperature about 40° C., spray air pressure about 1 kgf/cm$^2$, exhaust air gauge 100, BED pressure about 250 mmHg, rotor speed about 150 rpm, spray rate about 3.0 g/min and spray gun position lower side, mannitol was overcoated. The obtained fine granules were dried in vacuo at 40° C. for 16 hr and passed through a round sieve to give the outermost layer-coated fine granules with a particle size of 125 μm-500 μm.

[Composition in Mannitol-Overcoated Enteric Fine Granules (270 mg)]

| | |
|---|---|
| fine granules of Preparation Example 15 | 260 mg |
| mannitol | 10 mg |
| Total | 270 mg |

Preparation Example 17

Preparation of Granulated Powder for Outer Layer Component

Mannitol (414 g), low-substituted hydroxypropylcellulose (L-HPC-33, 60 g), crystalline cellulose (60 g) and crospovidone (30 g) were charged in a fluid bed granulator (LAB-1, manufactured by POWREX Corporation), and granulated while spraying an aqueous solution of mannitol (24 g) in purified water (136 g). The granules were dried to give a granulated powder for outer layer component (573 g).

Example 1

Preparation of Orally-Disintegrating Solid Preparation

The outermost layer-coated fine granules (45.9 g) obtained in Preparation Example 4, the enteric fine granules (27 g) obtained in Preparation Example 16, the granulated powder for outer layer component (79.4 g) obtained in Preparation Example 17 and magnesium stearate (1.6 g) were mixed in a bag to give a mixed powder. The obtained mixed powder (769.7 mg) was filled in a 13 mmφ flat-faced die with a beveled edge, and an orally-disintegrating solid preparation of the present invention (769.7 mg) containing compound X (30 mg) was prepared using Autograph (trade name, manufactured by SHIMADZU Corporation, tableting pressure: 2 ton/cm$^2$).

Example 2

Preparation of Orally-Disintegrating Solid Preparation

The outermost layer-coated fine granules (36.7 g) obtained in Preparation Example 6, the enteric fine granules (27 g) obtained in Preparation Example 16, the outer layer component-granulated powder (79.4 g) obtained in Preparation Example 17 and magnesium stearate (1.6 g) were mixed in a bag to give a mixed powder. The obtained mixed powder (723.4 mg) was filled in a 13 mmφ flat-faced die with a beveled edge, and an orally-disintegrating solid preparation of the present invention (723.4 mg) containing compound X (30 mg) was prepared using Autograph (trade name, manufactured by SHIMADZU Corporation, tableting pressure: 2 ton/cm$^2$).

INDUSTRIAL APPLICABILITY

The orally-disintegrating solid preparation of the present invention suppresses breakage of fine granules during tableting. In a solid preparation comprising fine granules containing a pharmaceutically active ingredient, particularly, a pharmaceutically active ingredient unstable to acid, the dissolution of the pharmaceutically active ingredient in the presence of acid, for example, in the stomach, can be improved to achieve a desired dissolution profile. In addition, variation of dissolution profiles for preparations or lots (dissolution variation) can also be improved. Since the preparation can control release of the pharmaceutically active ingredient for a long time, a therapeutically effective concentration can be maintained for a prolonged time, administration frequency can be reduced, an effective treatment with a small dose can be realized, and effects such as reduction of side effects caused by rise of blood concentration and the like can be achieved. Since the preparation shows superior disintegration property or dissolution property in the oral cavity, it is used for the treatment or prophylaxis of various diseases as a preparation conveniently taken by elderly persons and children even without water. In addition, since the fine granules comprising the pharmaceutically active ingredient having a size preventing powdery texture are blended, a preparation smooth in the mouth and comfortable during use can be provided.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

This application is based on a patent application No. 2006-356405 filed in Japan, the contents of which are incorporated in full herein by this reference.

The invention claimed is:

1. An orally-disintegrating solid preparation, comprising:
(1) fine granules A that release a pharmaceutically active ingredient in a manner of controlled release,
wherein the outermost layer of each of the fine granules A is further coated with a coating layer comprising hydroxypropylmethylcellulose and low-substituted hydroxypropylcellulose,
a weight ratio of the hydroxypropylmethylcellulose relative to the low-substituted hydroxypropylcellulose in the coating layer on the outermost layer of the fine granules is 1:10-10:1, and
the coating layer suppresses breakage of the fine granules A during tableting; and
(2) fine granules B that have a different release rate of a pharmaceutically active ingredient from that of the fine granules A of (1).

2. The preparation of claim 1, wherein the pharmaceutically active ingredient of the fine granules A and that of the fine granules B are the same.

3. The preparation of claim 1, wherein the fine granules B have a mean particle size of about 500 mm or below.

4. The preparation of claim 1, prepared using the fine granules B having a mean particle size of about 500 μm or below.

5. The preparation of claim 1, wherein the fine granules B comprise a core granule comprising a pharmaceutically active ingredient and an enteric coating layer formed thereon.

6. The preparation of claim 5, wherein the enteric coating layer of the fine granules B comprises a polymer substance that dissolves within a pH range of not less than 5.0 and not more than 6.0.

7. The preparation of claim 5, wherein the enteric coating layer of the fine granules B comprises one or more kinds of aqueous enteric polymer material selected from hydroxypropylmethylcellulose phthalate, cellulose acetate phthalate, hydroxypropylmethylcellulose acetate succinate, methacrylic acid copolymer, carboxymethylethylcellulose and shellac.

8. The preparation of claim 5, wherein the enteric coating layer of the fine granules B comprises a sustained-release material of a methacrylic acid copolymer.

9. The preparation of claim 1, further comprising an additive besides fine granules.

10. The preparation of claim 9, wherein the additive comprises a water-soluble sugar alcohol.

11. The preparation of claim 9, wherein the additive comprises a disintegrant.

12. The preparation of claim 9, wherein the fine granules A are comprised at 10-50 wt %, the fine granules B are comprised at 10-30 wt %, and the additive is comprised at 20-80 wt %, each relative to the whole preparation.

13. The preparation of claim 1, wherein the total weight of the preparation is about 1000 mg or below.

14. The preparation of claim 1, wherein the oral disintegration time is about 90 seconds or less.

15. The preparation of claim 1, wherein the fine granules A and the fine granules B comprise the pharmaceutically active ingredient at a weight ratio of 1:10-10:1.

* * * * *